(12) United States Patent
Van Den Hoef

(10) Patent No.: US 12,178,881 B2
(45) Date of Patent: Dec. 31, 2024

(54) FILTERABLE DUOCARMYCIN-CONTAINING ANTIBODY-DRUG CONJUGATE COMPOSITIONS AND RELATED METHODS

(71) Applicant: BYONDIS B.V., Nijmegen (NL)

(72) Inventor: Carolus Johannes Edgar Van Den Hoef, Nijmegen (NL)

(73) Assignee: Byondis B.V., Nijmegen (NL)

( * ) Notice: Subject to any disclaimer, the term of this patent is extended or adjusted under 35 U.S.C. 154(b) by 840 days.

(21) Appl. No.: 17/291,141

(22) PCT Filed: Nov. 4, 2019

(86) PCT No.: PCT/EP2019/080084
§ 371 (c)(1),
(2) Date: May 4, 2021

(87) PCT Pub. No.: WO2020/094561
PCT Pub. Date: May 14, 2020

(65) Prior Publication Data
US 2021/0386867 A1  Dec. 16, 2021

(30) Foreign Application Priority Data
Nov. 9, 2018 (EP) .................................... 18205459

(51) Int. Cl.
*A61K 47/68* (2017.01)
*A61K 9/19* (2006.01)
*A61K 47/12* (2006.01)
*A61K 47/16* (2006.01)

(52) U.S. Cl.
CPC ............ *A61K 47/6809* (2017.08); *A61K 9/19* (2013.01); *A61K 47/12* (2013.01); *A61K 47/16* (2013.01); *A61K 47/6803* (2017.08); *A61K 47/6855* (2017.08)

(58) Field of Classification Search
None
See application file for complete search history.

(56) References Cited

FOREIGN PATENT DOCUMENTS

| WO | WO2008/083312 | 7/2008 |
|---|---|---|
| WO | WO10/062171 | 6/2010 |
| WO | WO2011/133039 | 10/2011 |
| WO | WO2015095953 | 7/2015 |
| WO | WO2015/177360 | 11/2015 |

OTHER PUBLICATIONS

Dokter et al., Molecular Cancer Therapeutics, vol. 13, No. 11 (Nov. 1, 2014), pp. 2618-2629 (Year: 2014).*
Dokter et al., Supplement, (Nov. 1, 2014), pp. 1-10 (Year: 2014).*
Gong et al., AAPS Pharmscitech, vol. 19, No. 3 (Jan. 4, 2018) (Year: 2018).*

(Continued)

*Primary Examiner* — Karl J Puttlitz
(74) *Attorney, Agent, or Firm* — Buscher Patent PLLC

(57) ABSTRACT

Duocarmycin-based antibody-drug conjugates can be readily separated from non-conjugated duocarmycin linker-drug in a composition that contains a solvent system of water and acetonitrile and that has 30% to 60% acetonitrile.

15 Claims, 3 Drawing Sheets

(56) References Cited

OTHER PUBLICATIONS

Wagner-Rousset et al., MAbs. Jan. 1, 2014; 6(1): 173-184 (Year: 2014).*
Gu et al., Journal of Chromatography A, vol. 1393, May 8, 2015, pp. 81-88 (Year: 2015).*
He et al., Anal. Chem. 2017, 89, 5476-5483 (Year: 2017).*
Janeway et al., Immunobiology: The Immune System in Health and Disease. 5th edition. New York: Garland Science; 2001. The structure of a typical antibody molecule. Available from: https://www.ncbi.nlm.nih.gov/books/NBK27144/ downloaded May 23, 2024 (Year: 2001).*
P. M. LoRusso, et al., Clinical Cancer Research, (20), Oct. 15, 2011, pp. 6437-6447.
J. Katz, et al., Clinical Cancer Research, 17 (20), Oct. 15, 2011, pp. 6428-6436.
P. D. Senter, et al., Nature Biotechnology, Jul. 2012, 30 (7), 631-637.
C. R. Behrens and B. Liu, MAbs. Jan.-Feb. 2014, 6(1), 46-53.
M.M.C. van der Lee et al., Molecular Cancer Therapeutics, 2015, 14(3), 692-703.
J. Black et al., Molecular Cancer Therapeutics, 2016, 15 (8), 1900-1909.
ClinicalTrials.gov NCT02277717.
L. Chen et al., MAbs, 2016, 8 (7), 1210-1223.
W. Dokter et al., "Preclinical Profile of the HER2-Targeting ADC SYD983/SYD985: Introduction of a New Duocarmycin-Based Linker-Drug Platform", Molecular Cancer Therapeutics, vol. 13, No. 11, Nov. 1, 2014 (Nov. 1, 2014), p. 2618-2629.
W. Dokter et al., "Supplement—Preclinical profile of the HER2-targeting ADC SYD983/SYD985; introduction of a new duocarmycin-based linker-drug platform", Nov. 1, 2014 (Nov. 1, 2014), p. 1-10.
H. H. Gong et al., "Control Strategy for Small Molecule Impurities in Antibody-Drug Conjugates", AAPS Pharmscitech, Springer US, New York, vol. 19, No. 3, Jan. 4, 2018 (Jan. 4, 2018), p. 971-977.
J. He et al., "High-Resolution Accurate-Mass Mass Spectrometry Enabling In-Depth Characterization of in Vivo Biotransformations for Intact Antibody-Drug Conjugates," *Analytical Chemistry*, 2017, 89, pp. 5476-5483.

\* cited by examiner

FILTERABLE DUOCARMYCIN-CONTAINING ANTIBODY-DRUG CONJUGATE COMPOSITIONS AND RELATED METHODS

FIELD OF THE INVENTION

The present invention relates to compositions comprising duocarmycin-containing antibody-drug conjugates (ADCs) and optionally duocarmycin linker-drug in non-conjugated form. In particular, the compositions allow the ready filtration of the ADCs and separation from the duocarmycin linker-drug in a non-conjugated form (if present).

The present invention is further directed to methods for the composition preparation and for approving a duocarmycin-containing ADC batch.

BACKGROUND OF THE INVENTION

Monoclonal antibodies (mAbs) are one of the most important agents in the pharmaceutical industry. mAbs have also been conjugated to a variety of cytotoxic drugs to form antibody-drug conjugates or "ADCs." Generally, a linker connects the cytotoxic drug to the mAb. An ADC thus comprises a monoclonal antibody, a linker and a cytotoxic drug. The linker-drug can be conjugated to the antibody using side chains of either surface-exposed lysines (P. M. LoRusso et al., Clinical Cancer Research, 2011, 17 (20), 6437-6447) or free cysteines generated through reduction of interchain disulfide bonds (J. Katz et al., Clinical Cancer Research, 2011, 17 (20), 6428-6436; P. D Senter et al., Nature Biotechnology 2012, 30 (7), 631-637). Alternatively, the conjugation can be a site-specific conjugation through the side chains of an engineered cysteine residue in a suitable position of the mutated mAb (C. R. Behrens and B. Liu, MAbs, 2014, 6(1), 46-53).

Duocarmycins have been used as cytotoxic drugs in ADCs (WO2008/083312, WO2010/062171, WO2011/133039, WO2015/177360). Duocarmycins, first isolated from a culture broth of *Streptomyces* species, are members of a family of antitumor antibiotics that include duocarmycin A, duocarmycin SA, and CC-1065. Duocarmycins bind to the minor groove of DNA and subsequently cause irreversible alkylation of DNA. This disrupts the nucleic acid architecture, which eventually leads to tumour cell death.

In recent years, duocarmycin-containing ADCs such as trastuzumab duocarmazine (SYD985, trastuzumab vc-seco-DUBA), have been taken into preclinical and clinical development (M. M. C. van der Lee et al., Molecular Cancer Therapeutics, 2015, 14(3), 692-703; J. Black et al., Molecular Cancer Therapeutics, 2016, 15 (8), 1900-1909; ClinicalTrials.gov NCT02277717). Based on their potential antineoplastic activity further duocarmycin-containing ADCs are expected to be investigated.

In industrial processes for the production of ADCs, after the conjugation of the linker-drug to the mAb various purification steps are performed. Quality control procedures take place to ensure batch-to-batch reproducibility of these biotherapeutic molecules. Due to its toxicity, one of the impurities that must be strictly controlled in an ADC composition is the content of free linker-drug; that is linker-drug in non-conjugated form.

For the determination of the free linker-drug content, it has often been practised to first reduce the concentration of the ADC relative to the free linker-drug and then measure the amount of free linker-drug. Otherwise, the high concentration of the ADC makes determining the very low content of linker-drug difficult. In practical terms, the amount of ADC may be around 10 mg/ml while the amount of free linker-drug is normally less than 10 μg/ml, and often much less such as 0.2 μg/ml or 0.1 μg/ml. The large excess of ADC often masks the very small content (if any) of the free linker-drug in a usual chromatographic analytical technique; e.g., the very low concentration leads to the free linker-drug being obscured by other components and/or otherwise under the limit of detection.

Therefore, conventionally, the free linker-drug content can be determined by separating the ADC from the rest of the aqueous sample and then analysing the remainder of the sample for the presence of the (free) linker-drug. For example, direct filtration of the aqueous sample using centrifugal filtration with a filter having a molecular weight cutoff of about 30 kDa can often obtain a filtrate containing the free linker-drug while the ADC remains on the filter (see WO2015/095953, page 194, Cathepsin B linker cleavage assay). Alternatively, free linker-drug has been separated from the ADC by treating the sample with cold methanol and subjecting it to centrifugation so that the ADC will precipitate while the linker-drug in a non-conjugated form will stay in the supernatant (see L. Chen et al., MAbs, 2016, 8 (7), 1210-1223).

However, we found that duocarmycin linker-drugs presented unusual difficulties. The typical filtration procedure or direct precipitation as disclosed in the art failed to adequately separate the free duocarmycin linker-drug from the duocarmycin-containing ADC. For example, in the filtration process the free duocarmycin linker-drug tends to not pass through the filter into the filtrate but instead stays on the filter together with the duocarmycin-containing ADC. This leads to an insufficient amount of the free linker-drug being captured in the filtrate and renders the determination of the free linker-drug content inaccurate. Hence, there is a need for a method for separating free duocarmycin linker-drug from duocarmycin-containing ADCs. Similarly, there is a need for a method for detecting and quantifying duocarmycin linker-drug in a sample comprising duocarmycin-containing ADCs and duocarmycin linker-drug (if present).

SUMMARY OF THE INVENTION

The present invention is based in part on the discovery that acetonitrile can aid in the separation of duocarmycin linker-drug in a non-conjugated form from a duocarmycin-containing ADC via filtration.

Accordingly, a first aspect of the invention relates to a composition, comprising (a) a solvent system containing water and acetonitrile; (b) an acid; (c) an antibody-drug conjugate of formula (I):

wherein Ab is an antibody or an antigen-binding fragment thereof, L-D is a duocarmycin linker-drug and m represents an average DAR of from 1 to 12; and optionally (d) the duocarmycin linker-drug in non-conjugated form;

wherein said composition comprises 30% to 60% (v/v) of said acetonitrile, preferably 35% to 55% of said acetonitrile.

Another aspect of the invention relates to a method, which comprises combining (i) an aqueous solution or a lyophilized product of an antibody-drug conjugate of formula (I):

wherein Ab is an antibody or an antigen-binding fragment thereof, L-D is a duocarmycin linker-drug and m represents an average DAR of from 1 to 12, and optionally further comprising the duocarmycin linker-drug in non-conjugated form, with (ii) a dilution medium that comprises water, acetonitrile, and acid to form a composition, wherein said composition comprises 30% to 60% (v/v), preferably 35% to 55%, of said acetonitrile.

A further aspect of the invention relates to a method of releasing/approving an antibody-drug conjugate batch, which comprises:

1) Obtaining a sample from an antibody-drug conjugate batch, wherein said batch comprises an antibody conjugated with a duocarmycin linker-drug and optionally duocarmycin linker-drug in non-conjugated form;
2) Combining said sample with a dilution medium which comprises water, acetonitrile, and acid to form a filterable composition which comprises 30% to 60% (v/v), preferably 35% to 55%, of said acetonitrile;
3) Filtering said filterable composition to obtain a filtrate that is substantially free of said antibody-drug conjugate;
4) Analysing said filtrate and determining whether said filtrate contains said duocarmycin linker-drug in non-conjugated form below a predetermined level; and
5) Releasing/approving said antibody-drug conjugate batch if said duocarmycin linker-drug in non-conjugated form is below said predetermined level.

DETAILED DESCRIPTION OF THE INVENTION

Figure 1:
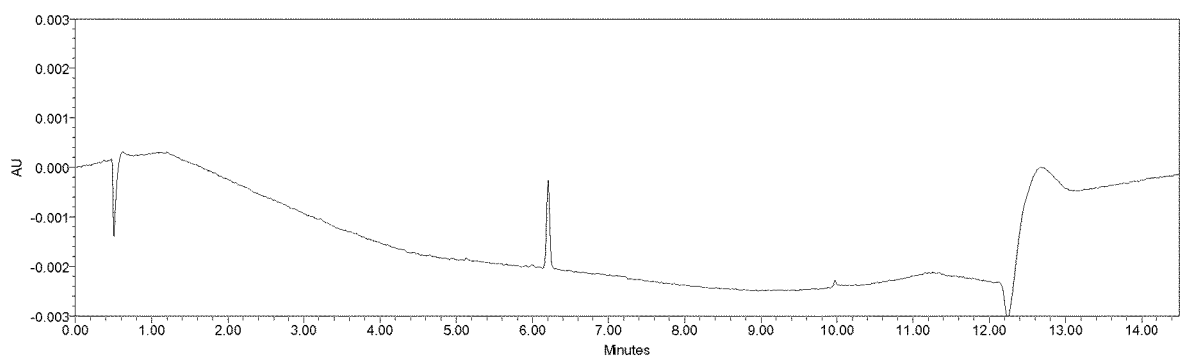
FIG. 1 represents the chromatogram of a non-conjugated duocarmycin linker-drug, vc-seco-DUBA, in accordance with Example 1.

The present invention relates to a composition, comprising (a) a solvent system containing water and acetonitrile; (b) an acid; (c) an antibody-drug conjugate of formula (I):

$$Ab\text{-}(L\text{-}D)_m \qquad (I),$$

wherein Ab is an antibody or an antigen-binding fragment thereof, L-D is a duocarmycin linker-drug and m represents an average drug-to-antibody ratio (DAR) of from 1 to 12; and optionally (d) the duocarmycin linker-drug in non-conjugated form;
wherein said composition comprises 30% to 60% (v/v), preferably 35% to 55%, of said acetonitrile.

The solvent system used in the present invention contains water and acetonitrile. As used herein the term "solvent system" refers to a mixture of solvents that can dissolve the duocarmycin linker-drug in a non-conjugated form. Typically, the solvent system consists of water and acetonitrile, but additional solvents can be present in some embodiments. For example, other water-miscible organic solvents such as $C_1$-$C_6$ alcohols (e.g., methanol or ethanol) or polyols could optionally be present. Generally, any additional solvents comprise less than 20% (v/v); typically, less than 10%; and often less than 5% of the composition. Usually the solvent system consists of water and acetonitrile. The water is not particularly limited in terms of quality, though for practical reasons relatively pure water is advantageously used such as DI water and more preferably Milli-Q water.

The acetonitrile is used in a concentration of from 30% to 60% (v/v). A concentration above 60% tends to cause too much leakage of the duocarmycin-containing ADC through the filter. Such leakage would cause the filtrate to have too high a concentration of ADC compared to the low concentration of free linker-drug and thus interfere with accurate determinations of the amount of free linker-drug; e.g. masking. Generally, the amount of leakage is too high when more than 1.0% of the ADC in the sample passes into the filtrate and typically no more than 0.5% is acceptable. Often, when leakage is present, the amount of ADC that passes into the filtrate is 0.3% or less, more often 0.2% or less, and usually 0.1% or less. On the other hand, a concentration of acetonitrile below 30% tends to cause insufficient separation; i.e., the duocarmycin linker-drug in non-conjugated form (mostly) does not pass through the filter and hence a failure to separate. Without wishing to be bound by theory, the inventors theorize that hydrophobic interactions between the duocarmycin linker-drug (in a non-conjugated form) and the duocarmycin-containing ADC prevents or retards the separation. Adding sufficient amounts of acetonitrile as part of the solvent system allows these forces to be sufficiently overcome to more readily permit the separation by filtration. By not adding too much acetonitrile, damage to the filter is avoided and leakage of the duocarmycin-containing ADC is minimized or prevented. Moreover, the acetonitrile in a concentration of from 30% to 60% (v/v) does not influence the stability of either the ADC, the antibody or the duocarmycin linker-drug. Thus, the inventors surprisingly found that free duocarmycin linker-drug can be easily and efficiently filtrated when placed in a composition that comprises water, acid and acetonitrile in a concentration of from 30% to 60% (v/v), preferably of from 35% to 55%, most preferably of 40%.

Suitable acids for use in the present invention are organic acids or inorganic mineral acids. Typically, the acid for use in the present invention is selected from the group consisting of trifluoroacetic acid, formic acid and hydrochloric acid. The amount of the acid is not critical, merely that the composition is acidic, even if only slightly. Typically, the acid is used so that the composition has a pH below 7. The composition may have acid in a concentration of from 0.01% to 5% (v/v), or of from 0.05% to 2%, or of from 0.05% to 1.5%, or of from 0.1% to 1%.

The ADC content is not particularly limited in the composition of the present invention. Typically, the composition contains the ADC in a concentration of from 0.1 to 100 mg/ml, more typically of from 0.5 to 50 mg/ml, and usually of from 1.0 to 10 mg/ml. The amount of non-conjugated (free) duocarmycin linker-drug is typically 0 to 100 µg/ml, more typically 0 to 10 µg/ml, and often 0 to 1 µg/ml. In many embodiments, the ADC concentration is at least 1,000 times greater than the concentration of free duocarmycin linker-drug.

The composition may contain additional ingredients. For example, buffers and/or salts, such as those commonly used in column chromatography or UF/DF, or sugars such as mannitol and/or other excipients that may be present in a finished dosage form also known as drug product.

In the ADCs of formula (I), Ab can be any antibody or antigen-binding fragment thereof, e.g. a F(ab')₂ or a Fab' fragment, a single chain (sc) antibody, a scFv, a single domain (sd) antibody, a diabody, or a minibody. Generally, the antibody or any antigen-binding fragment thereof is one that has a therapeutic activity, but such independent efficacy is not necessarily required, as is known in the art of ADCs. Antibodies may be of any isotype such as IgG, IgA or IgM antibodies. Preferably, the antibody is an IgG antibody, more preferably an IgG$_1$ or IgG$_2$ antibody. The antibodies may be chimeric, humanized or human. Preferably, the antibodies are humanized. Even more preferably, the antibody is a humanized or human IgG antibody, most preferably a humanized or human IgG$_1$ monoclonal antibody (mAb). Preferably, said antibody has κ (kappa) light chains, i.e., a humanized or human IgG$_1$-κ antibody.

For clarity, a "humanized" antibody refers to an antibody having the antigen-binding complementarity determining regions (CDRs) derived from antibodies from a non-human species, commonly mouse, rat or rabbit, but have a framework that is at least partially human. For instance, the non-human CDRs may be placed within a human framework (framework region (FR) FR1, FR2, FR3 and FR4) of the variable regions of the heavy chain (HC) and light chain (LC); i.e., a fully human framework supporting the non-human CDRs. However, selected amino acids in the human FRs may be exchanged for the corresponding non-human framework amino acids, e.g., to improve binding affinity, while retaining low immunogenicity. Going further, the non-human frameworks can be largely retained and only selected amino acids of the non-human species FRs may be exchanged for their corresponding human amino acids to reduce immunogenicity, while retaining the antibody's binding affinity. All of these options are considered to be "humanized" variable regions for purposes of the present invention. The thus humanized variable regions are combined with human constant regions to form a humanized antibody.

These antibodies may be produced recombinantly, synthetically, or by other suitable methods known in the art.

The antibody can be monospecific (i.e. specific for one antigen; such antigen may be common between species or have similar amino acid sequences between species) or bispecific (i.e. specific for two different antigens of a species) and comprises at least one HC and LC variable region binding to a target selected from the group consisting of: annexin A1, B7H4, CA6, CA9, CA15-3, CA19-9, CA27-29, CA125, CA242 (cancer antigen 242), CCR2, CCR5, CD2, CD19, CD20, CD22, CD30 (tumour necrosis factor 8), CD33, CD37, CD38 (cyclic ADP ribose hydrolase), CD40, CD44, CD47 (integrin associated protein), CD56 (neural cell adhesion molecule), CD70, CD74, CD79, CD115 (colony stimulating factor 1 receptor), CD123 (interleukin-3 receptor), CD138 (Syndecan 1), CD203c (ENPP3), CD303, CD333, CEA, CEACAM, CLCA-1 (C-type lectin-like molecule-1), CLL-1, c-MET (hepatocyte growth factor receptor), Cripto, DLL3, EGFL, EGFR, EPCAM, EPh (e.g. EphA2 or EphB3), ETBR (endothelin type B receptor), FAP, FcRL5 (Fc receptor-like protein 5, CD307), FGFR (e.g. FGFR3), FOLR1 (folate receptor alpha), GCC (guanylyl cyclase C), GPNMB, HER2, HMW-MAA (high molecular weight melanoma-associated antigen), integrin α (e.g. αvβ3 and αvβ5), IGF1R, TM4SF1 (or L6 antigen), Lewis A like carbohydrate, Lewis X, Lewis Y (CD174), LIV1, mesothelin (MSLN), MN (CA9), MUC1, MUC16, NaPi2b, Nectin-4, PD-1, PD-L1, PSMA, PTK7, SLC44A4, STEAP-1, 5T4 antigen (or TPBG, trophoblast glycoprotein), TF (tissue factor, thromboplastin, CD142), TF-Ag, Tag72, TNFR, TROP2 (tumour-associated calcium signal transducer 2), VEGFR and VLA.

Examples of suitable antibodies include blinatumomab (CD19), epratuzumab (CD22), iratumumab and brentuximab (CD30), vadastuximab (CD33), tetulumab (CD37), isatuximab (CD38), bivatuzumab (CD44), lorvotuzumab (CD56), vorsetuzumab (CD70), milatuzumab (CD74), polatuzumab (CD79), rovalpituzumab (DLL3), futuximab (EGFR), oportuzumab (EPCAM), farletuzumab (FOLR1), glembatumumab (GPNMB), trastuzumab and pertuzumab (HER2), etaracizumab (integrin), anetumab (mesothelin), pankomab (MUC1), enfortumab (Nectin-4), and H8, A1, and A3 (5T4 antigen).

In a preferred embodiment, Ab in the compound of formula (I) is an anti-HER2 antibody, even more preferred Ab is the anti-HER2 antibody trastuzumab.

In the context of the present invention, -L-D in the compound of formula (I) may be any duocarmycin linker-drug moiety. The duocarmycin moiety is preferably represented by one of the following formulas:

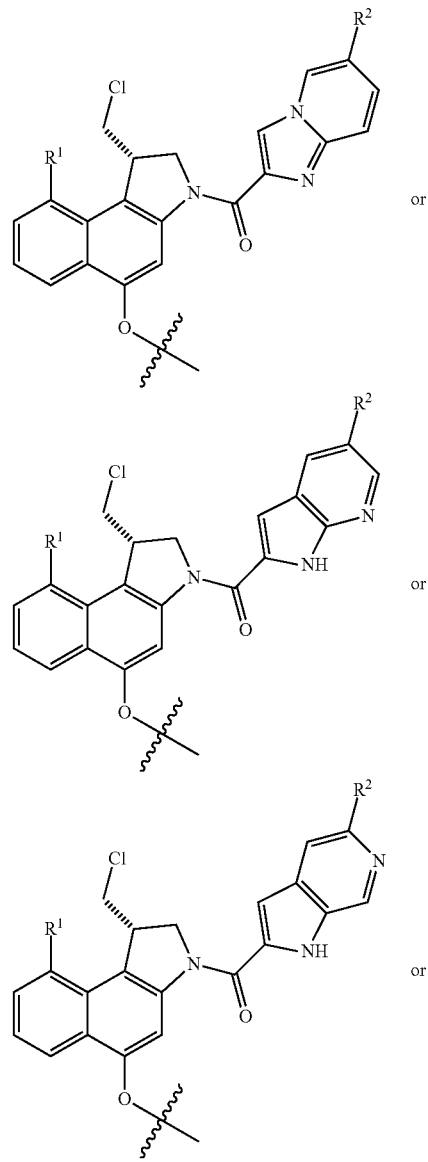

-continued

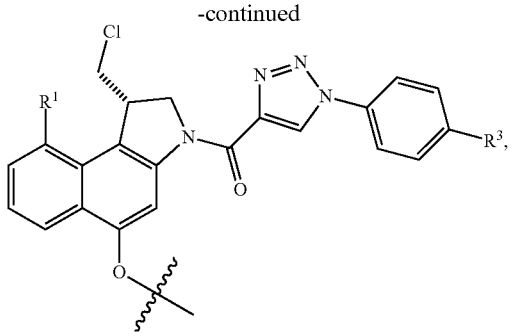

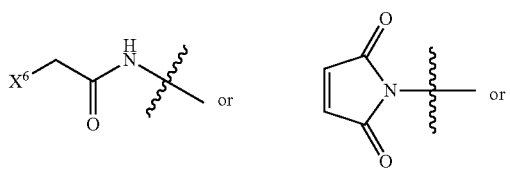

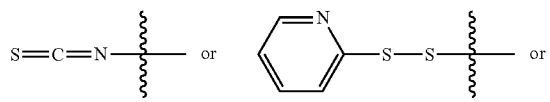

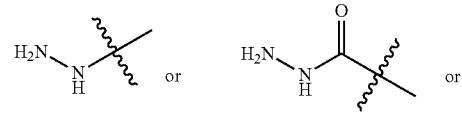

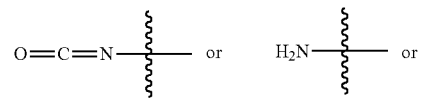

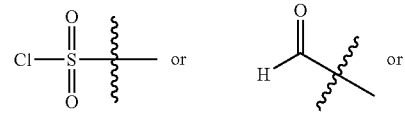

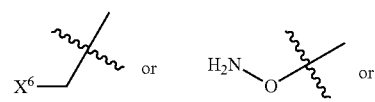

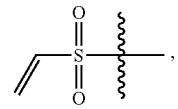

wherein $R^1$, $R^2$, and $R^3$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, $N(R^a)C(O)N(R^b)R^c$, and a water-soluble group, wherein $R^a$, $R^b$, and $R^c$ are independently selected from H and optionally substituted $(CH_2CH_2O)_{aa}CH_2CH_2X^1R^{a1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein aa is selected from 1 to 1000, $X^1$ is selected from O, S, and $NR^{b1}$, and $R^{b1}$ and $R^{a1}$ are independently selected from H and $C_{1-3}$ alkyl, and further provided that one or more of the optional substituents in $R^a$, $R^b$, and/or $R^c$ may optionally be a water-soluble group and two or more of $R^a$, $R^b$, and $R^c$ optionally may be joined by one or more bonds to form one or more optionally substituted carbocycles and/or heterocycles.

The linker moiety (-L-) can be any known or suitable moiety for attaching the drug to the antibody or antigen binding fragment thereof. Generally, the linker is cleavable under certain conditions, so as to release the drug from the antibody as is known in the art.

The end of the linker that will be bonded to the antibody (or fragment thereof) typically contains a functional group that can react with the natural or non-natural amino acid of the Ab under relatively mild conditions. This functional group is referred to herein as a reactive moiety (RM). Examples of reactive moieties include, but are not limited to, carbamoyl halide, acyl halide, active ester, anhydride, α-halo acetyl, α-halo acetamide, maleimide, isocyanate, isothiocyanate, disulfide, thiol, hydrazine, hydrazide, sulfonyl chloride, aldehyde, methyl ketone, vinyl sulfone, halo methyl, and methyl sulfonate.

In a preferred embodiment of the present invention RM is

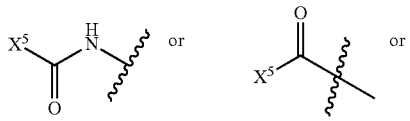

wherein $X^5$ is selected from —Cl, —Br, —I, —F, —OH, —O—N-succinimide, —O-(4-nitrophenyl), —O-pentafluorophenyl, —O-tetrafluorophenyl, —O—C(O)—$R^4$, and —O—C(O)—$OR^4$;

$X^6$ is selected from —Cl, —Br, —I, —O-mesyl, —O-triflyl, and —O-tosyl;

$R^4$ is branched or unbranched $C_1$-$C_{10}$ alkyl or aryl.

The duocarmycin linker-drug can be expressed in conjugated form (-L-D) or non-conjugated form (L-D) also referred to as "free" linker-drug. Accordingly, the following formulas (II) and (IV) represent preferred duocarmycin linker-drugs in conjugated and non-conjugated forms, respectively. Similarly, formulas (III) and (V) represent alternative preferred duocarmycin linker-drugs in conjugated and non-conjugated form, respectively:

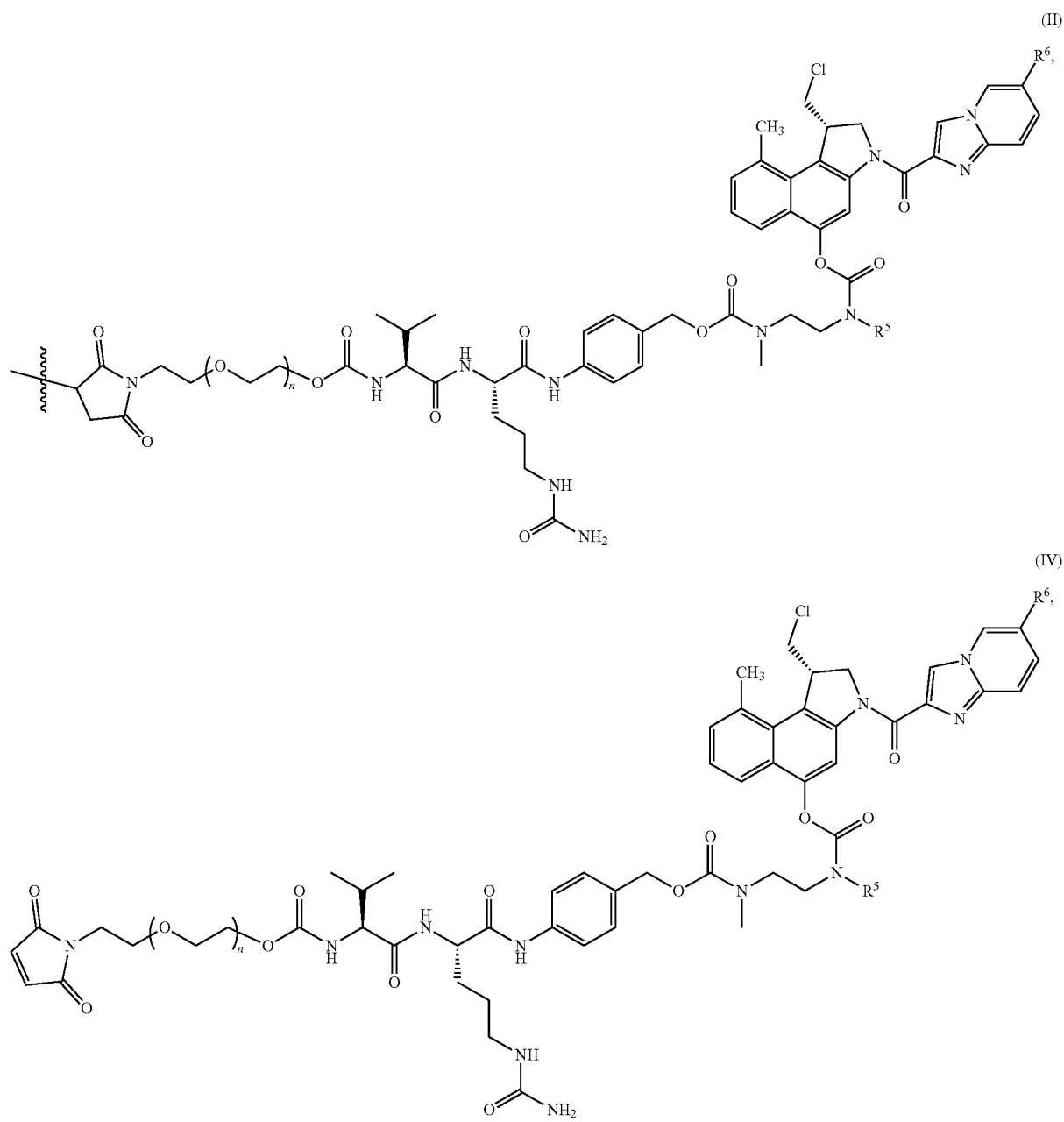
wherein
n is 0-3,
R⁵ is selected from
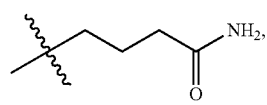
-continued
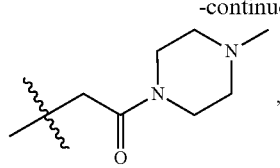
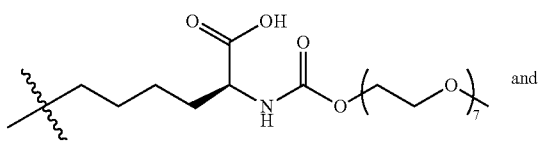
and

11
-continued
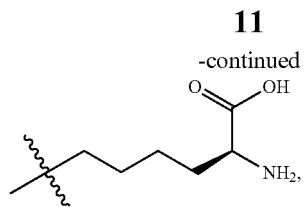
y is 1-16, and
R⁶ is selected from
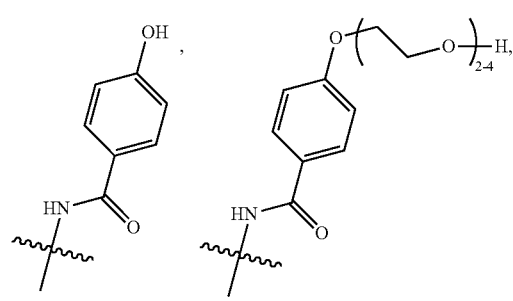
12
-continued
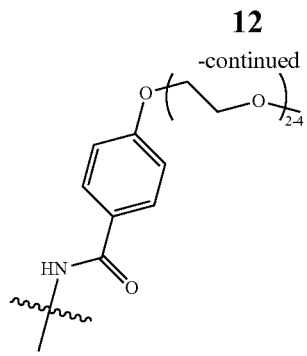
and
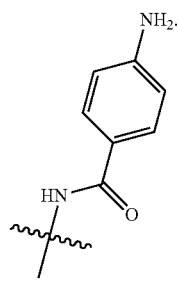
The alternative duocarmycin linker-drugs represented by formula (III) for conjugated and formula (V) for non-conjugated forms are set forth below:
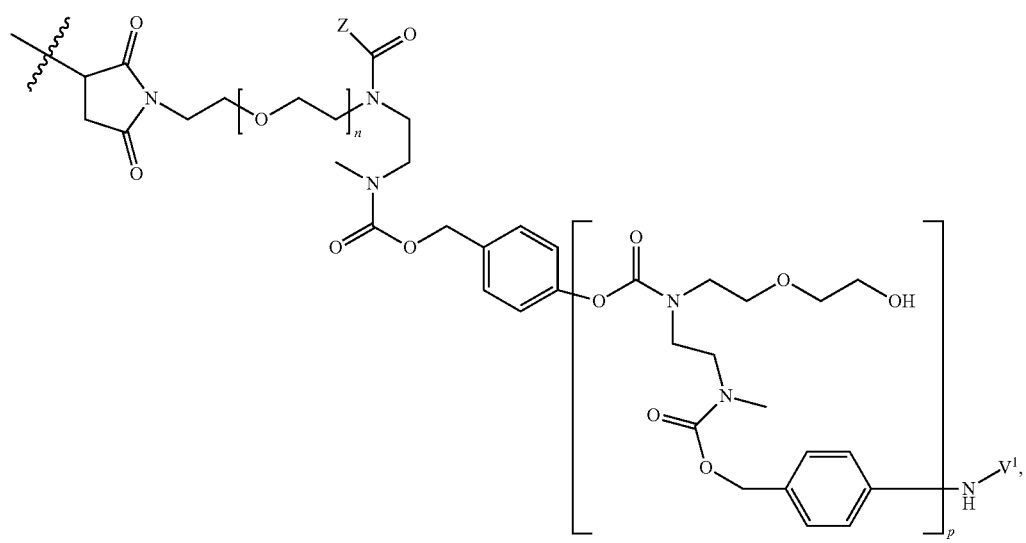

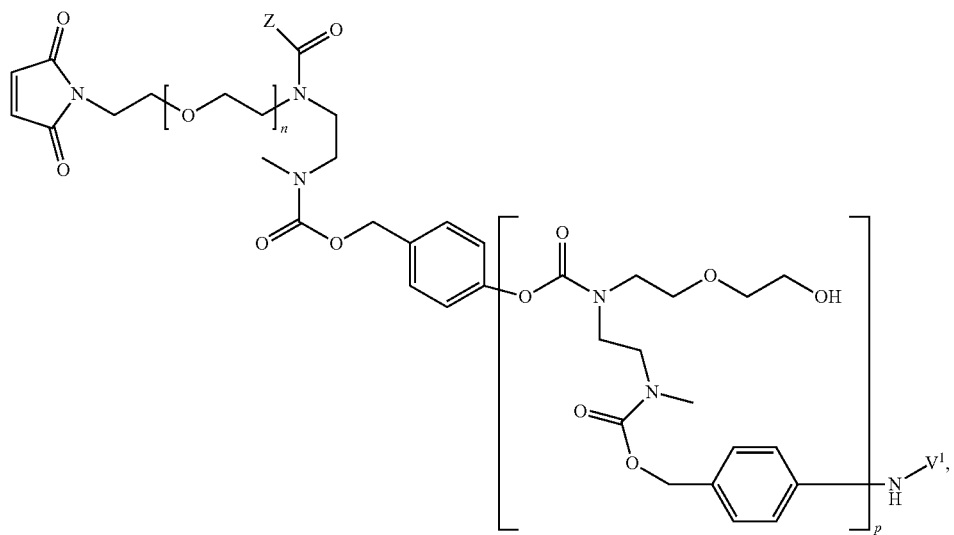

(V)

wherein

V¹ is a conditionally-cleavable or conditionally-transformable moiety, which can be cleaved or transformed by a chemical, photochemical, physical, biological, or enzymatic process; Z is a duocarmycin derivative, n is 0, 1, 2, or 3; and p is 0 or 1.

Preferably, Z is a duocarmycin moiety of the formula:

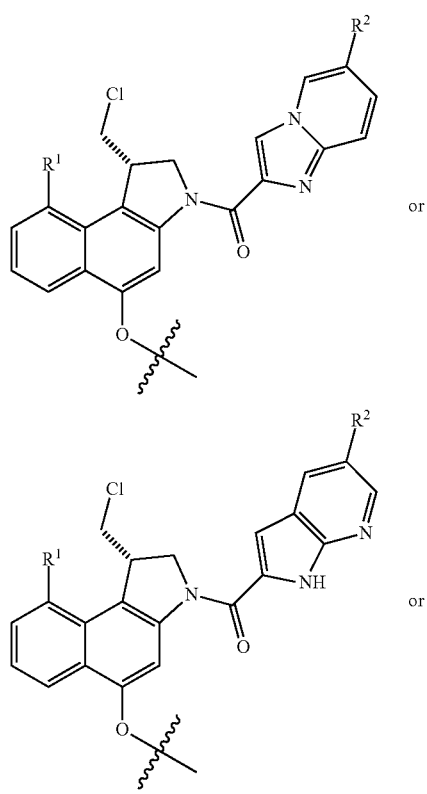

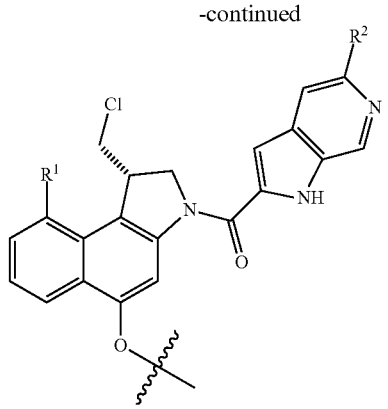

or

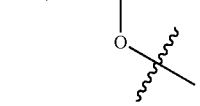

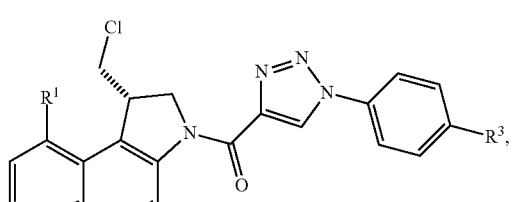

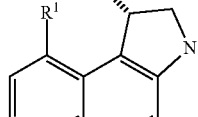

or

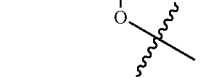

as described (and defined) above. Specific examples of such duocarmycin moieties (e.g., Z) for use in the present invention include:

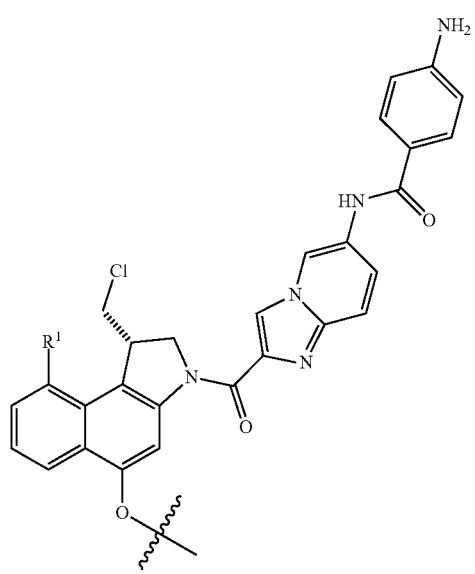
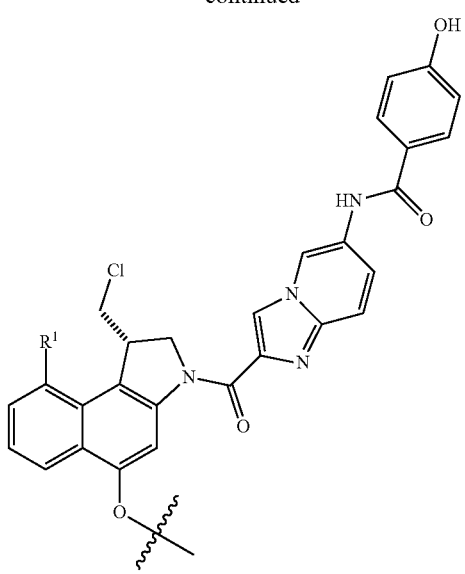
or
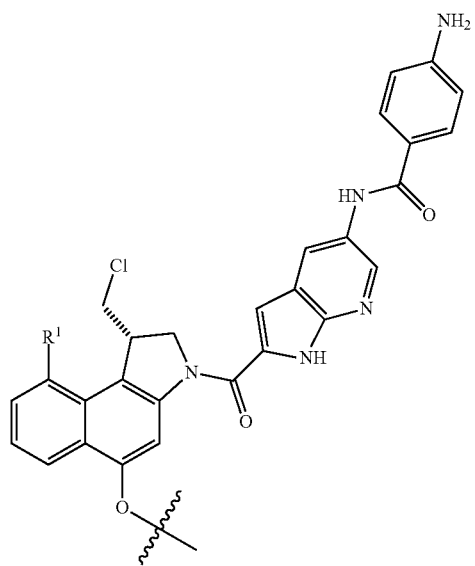
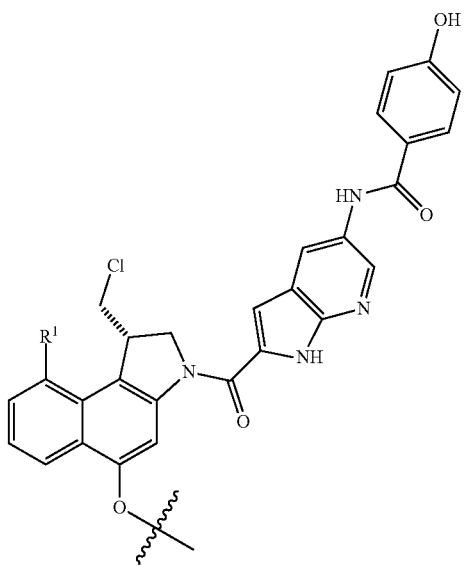
or
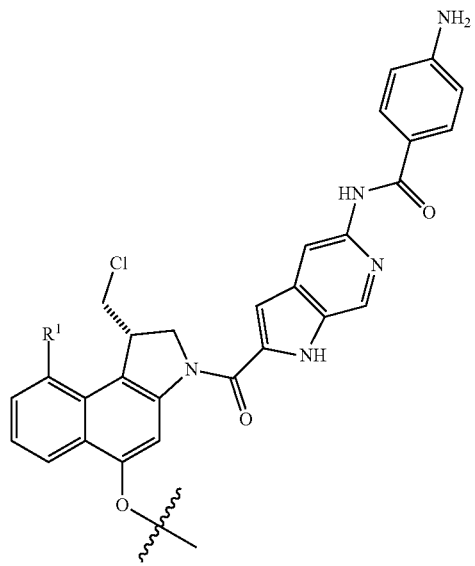
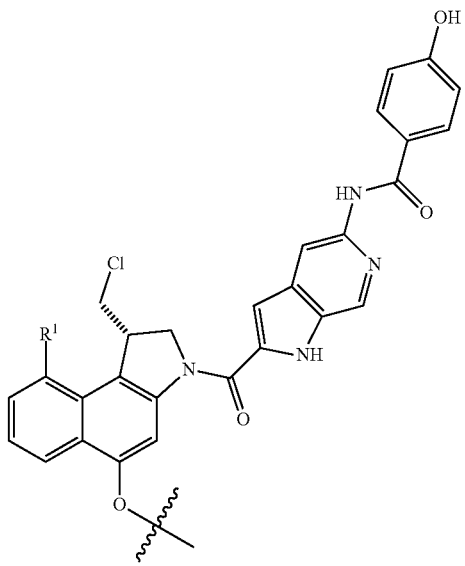
or

17
-continued
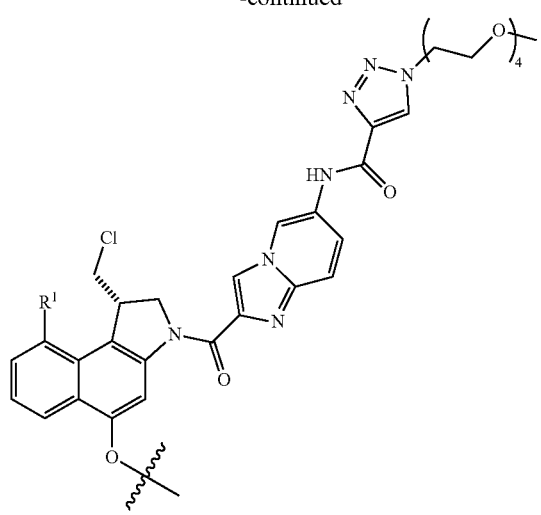
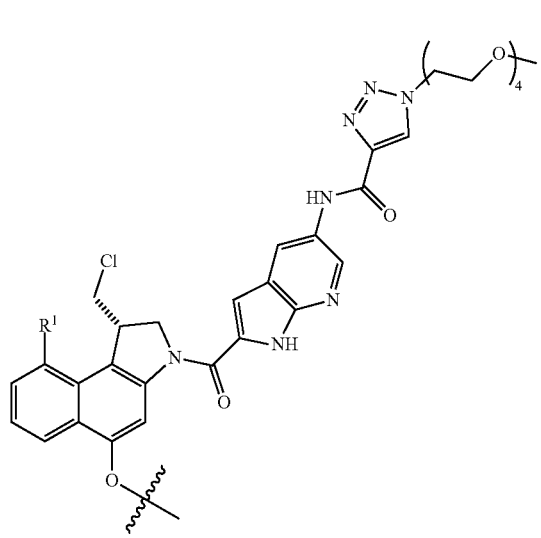
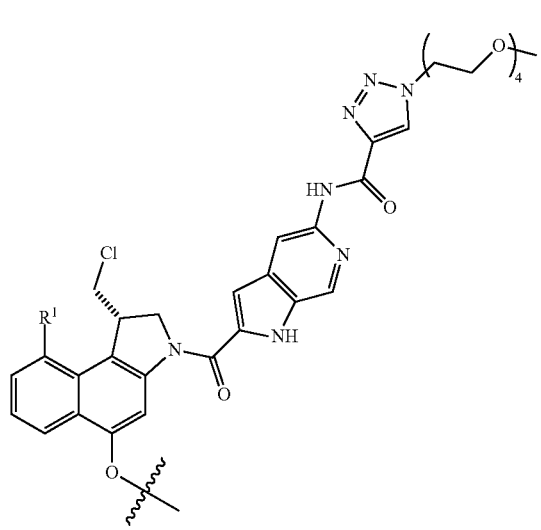
18
-continued
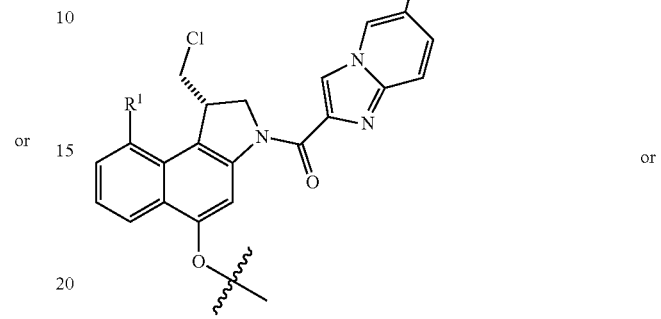
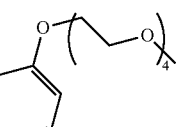
or
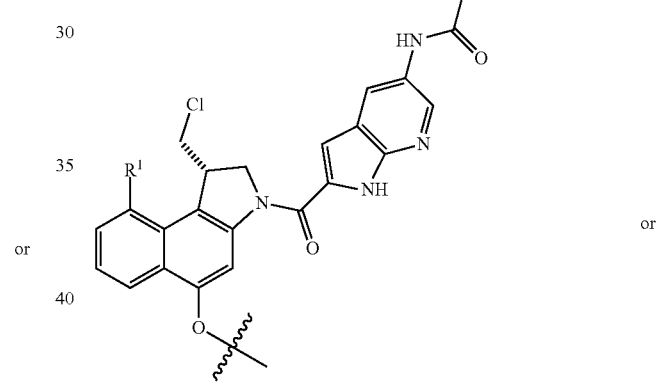
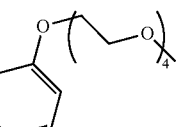
or
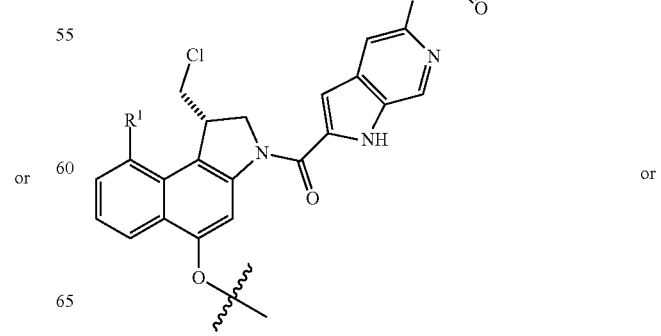
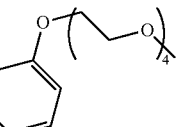
or

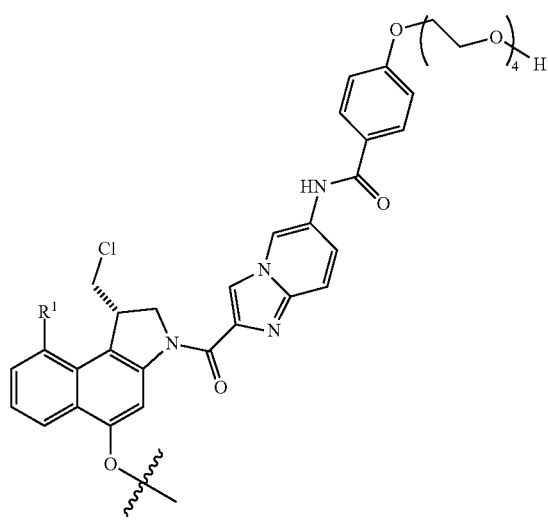
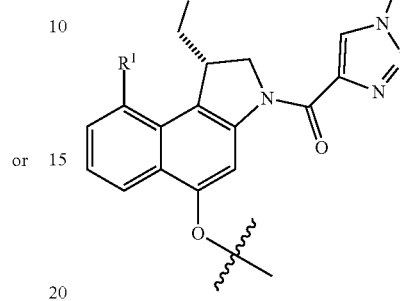
or
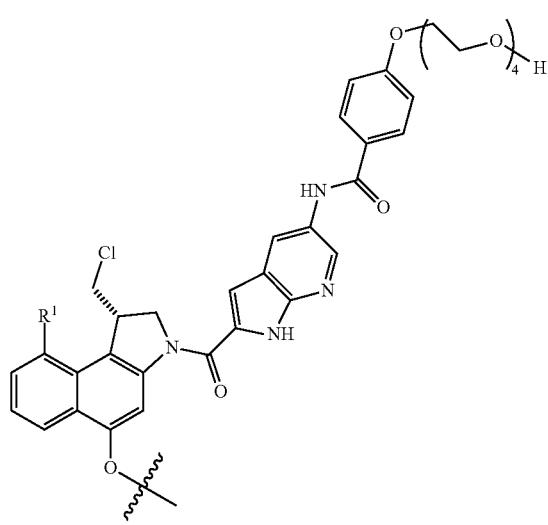
or
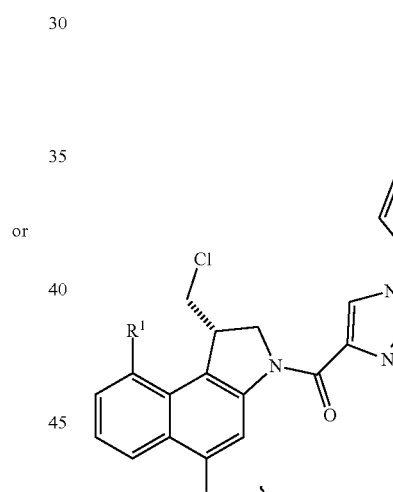
or
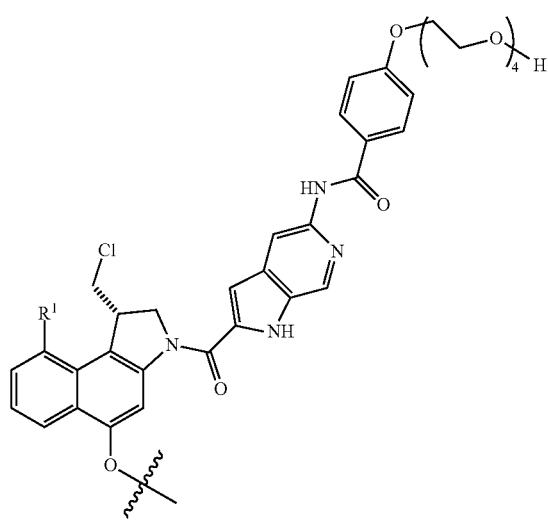
or
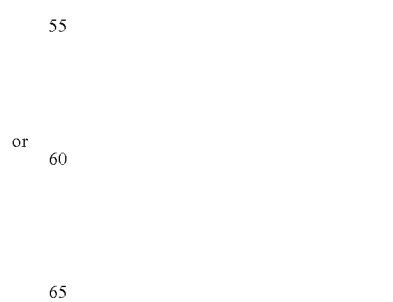
A particularly preferred species of duocarmycin linker-drug is shown below in conjugated form:

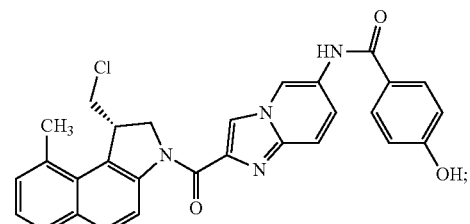
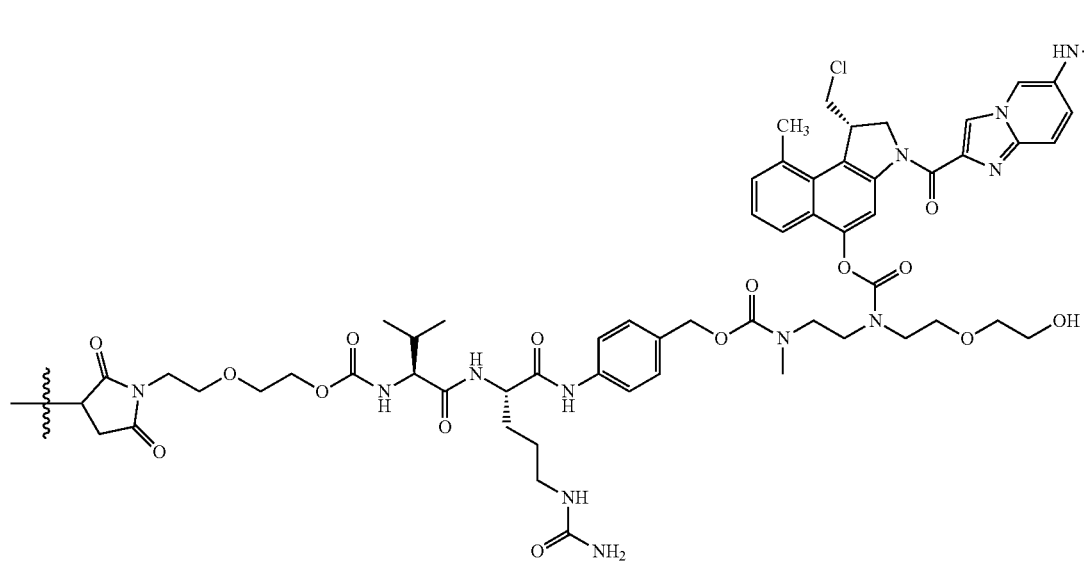
and in the corresponding non-conjugated form (i.e. vc-seco-DUBA):
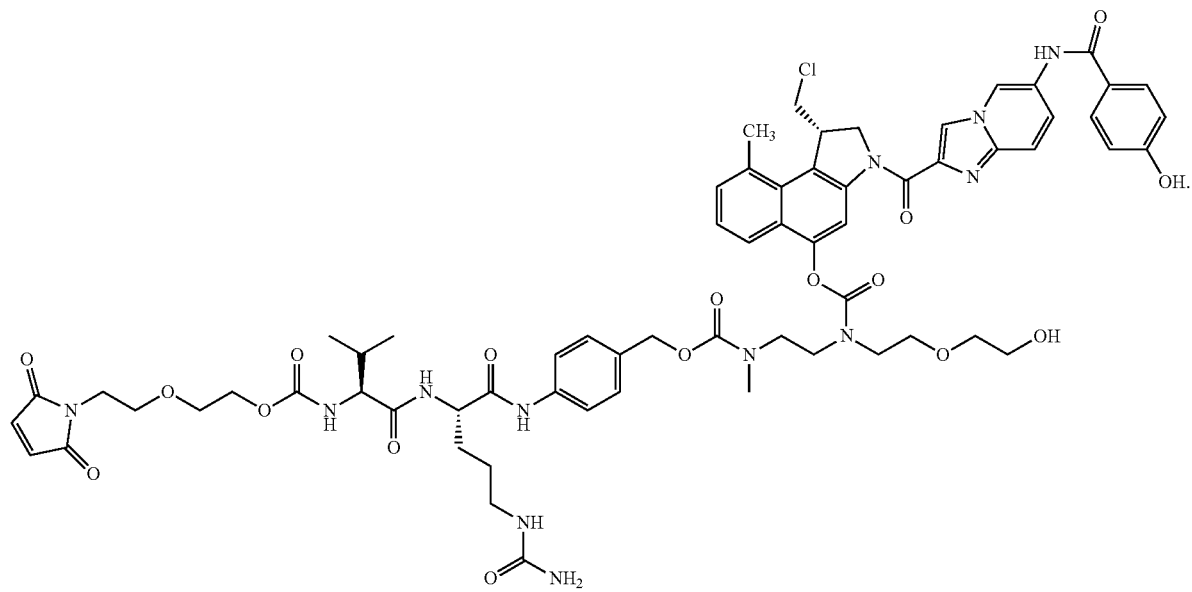 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCN4C(=O)C=CC4=O)C(C)C)cc3)cc3c(c12)[C@H](CCl)CN3C(=O)c1cn2cc(NC(=O)c3ccc(O)cc3)ccc2n1]
For brevity sake, the following species of duocarmycin linker-drug are shown only in conjugated form, but it should be understood that the corresponding non-conjugated form is also contemplated as would be understood by a worker skilled in the art:

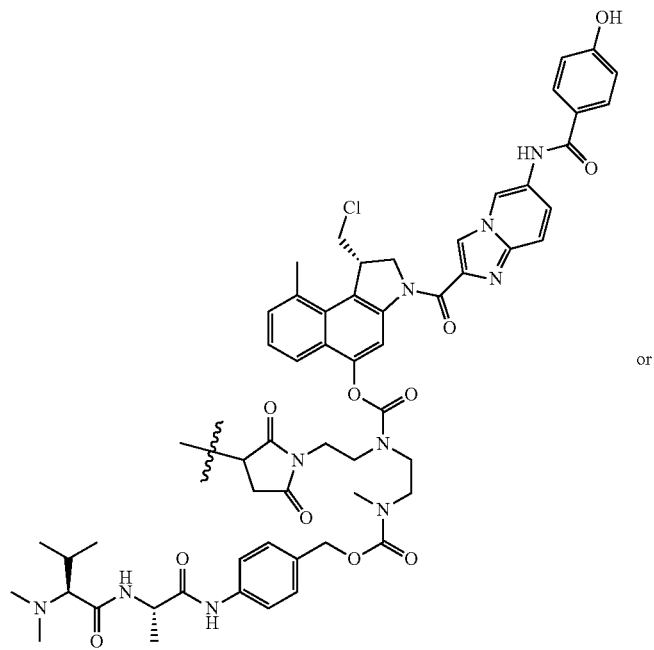
or
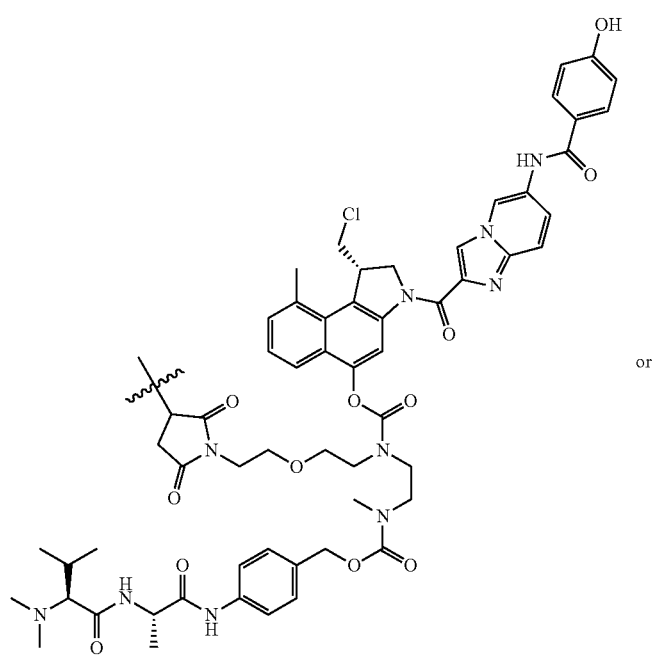
or

-continued
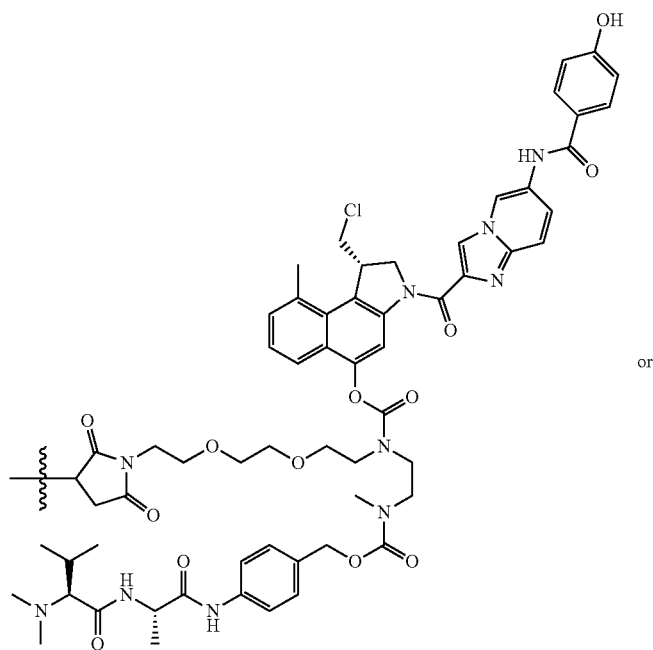
or
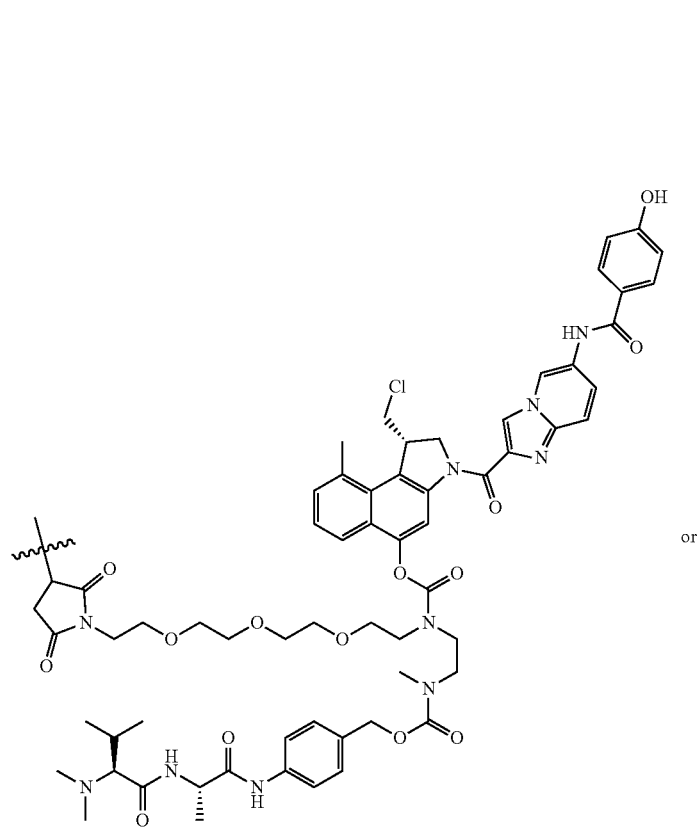
or

-continued
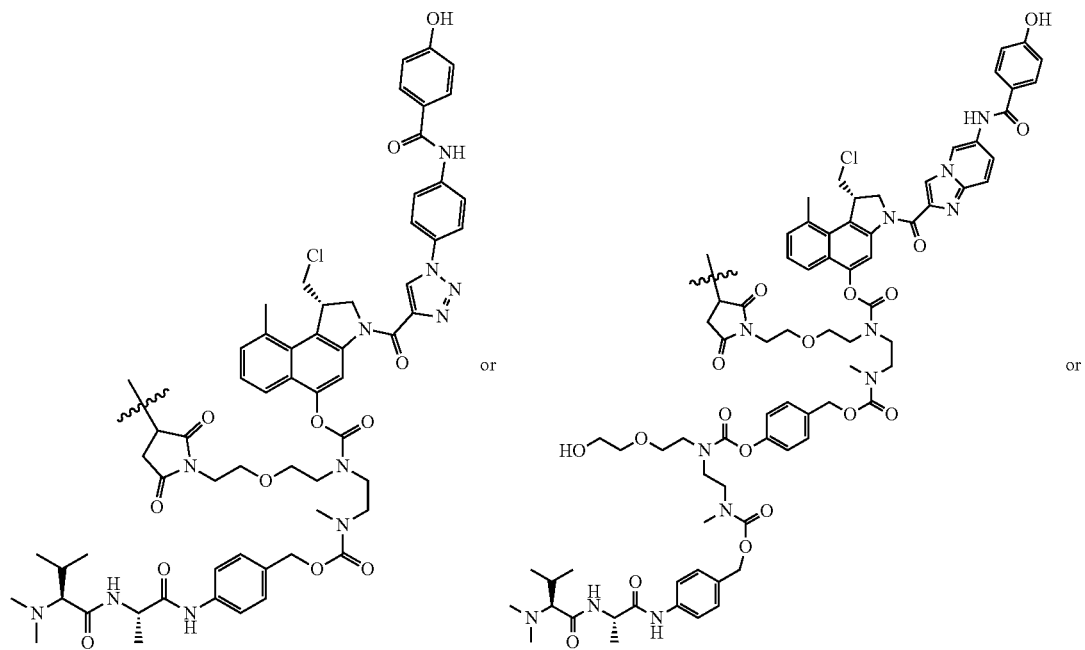
or
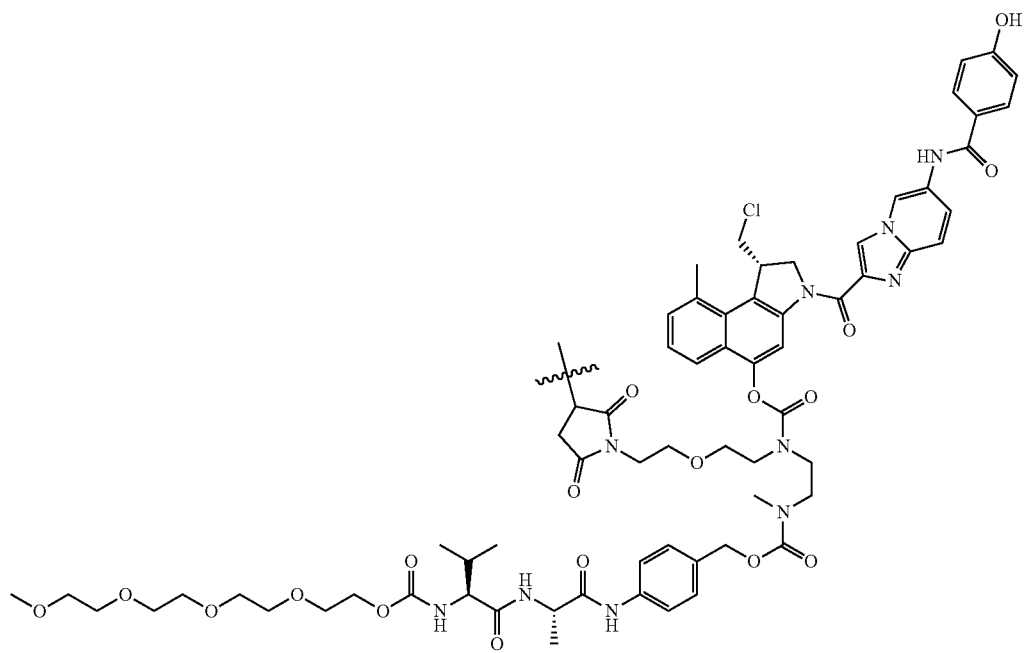

-continued
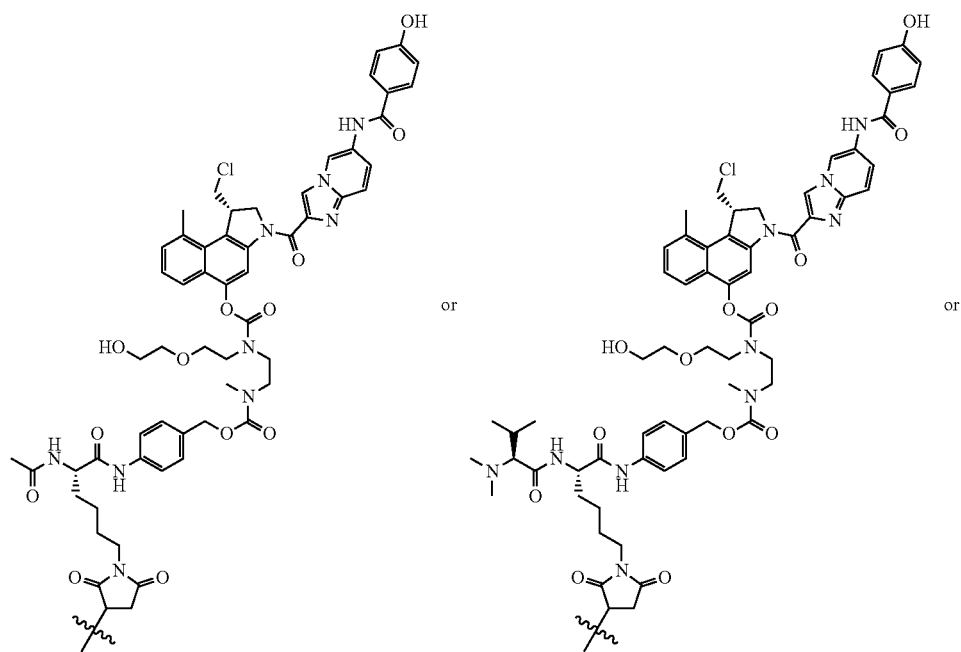
or
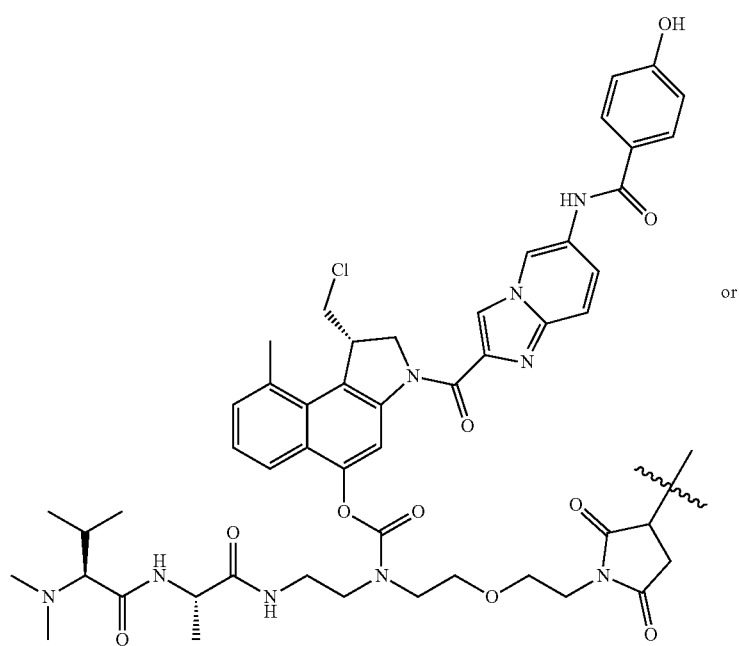
or

-continued

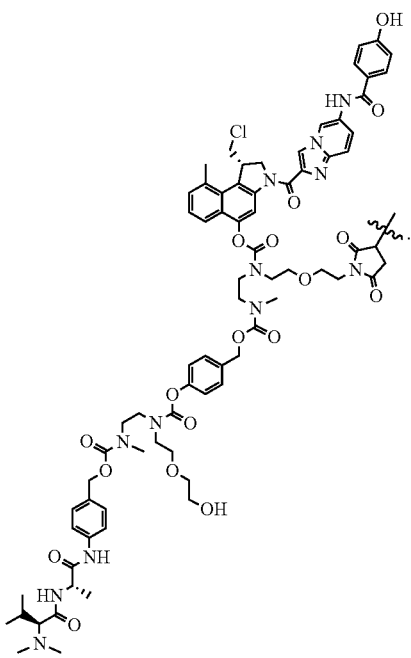 [SMILES: *C1CC(=O)N(CCOCCN(CCN(C)C(=O)OCc2ccc(OC(=O)N(CCOCCO)CCN(C)C(=O)OCc3ccc(NC(=O)[C@H](C)NC(=O)[C@H](C(C)C)N(C)C)cc3)cc2)C(=O)Oc2cc3c(c4c(C)cccc24)[C@H](CCl)CN3C(=O)c2cn3cc(NC(=O)c4ccc(O)cc4)ccc3n2)C1=O]

The composition of the present invention is useful in facilitating the separation via mere filtration of the duocarmycin-containing ADC from the free duocarmycin linker-drug. Such a separation permits analysis of the filtrate for very small amounts of free linker-drug without the burden of large amounts of ADC. In a broader sense, the composition of the present invention makes checking for the presence and/or amount of the free linker-drug in an ADC composition more accurate, convenient, and practical.

The detection and/or quantitation of the amount of free duocarmycin linker-drug can be useful in various roles, including development of a robust ADC purification process, quality control of the ADC drug substance or drug product, and stability testing of drug substance or drug product, to name a few applications. It should be understood that in most pharmaceutical applications of an ADC, the intent is to have little to no free linker-drug present. The duocarmycin drug is potent. When conjugated to an antibody, or antigen binding fragment thereof, the duocarmycin drug is delivered as a cytotoxic payload to the antibody-targeted site. As a free duocarmycin linker-drug, however, random healthy cells could be disrupted; hence the need to strictly control the amount of free duocarmycin linker-drug to low levels. Supplying the duocarmycin-containing ADC with significant amounts of free duocarmycin linker-drug could cause unacceptable risks to patients. Accordingly, the free duocarmycin linker-drug is only optionally present in the filterable composition of the invention as the purification protocol has hopefully removed all of the free linker-drug. Whether present or not, it is important to have a method that can confirm the absence and/or quantify the amount of the free duocarmycin linker-drug (if present) in the ADC composition to very low levels of detection.

The composition of the present invention can be prepared by any method that combines the solvents, acid, and ADC. The order of addition of the ingredients and whether done sequentially or simultaneously are not limited. Frequently, however, the ADC in the form of an aqueous solution or a lyophilized product is combined with a dilution medium that contains water, acetonitrile, and acid in order to form the filterable composition of the present invention.

Accordingly, another aspect of the invention relates to a method, which comprises combining (i) an aqueous solution (or a lyophilized product) of the ADC of formula (I):

$$Ab\text{-}(L\text{-}D)_m \quad (I),$$

optionally further comprising the corresponding duocarmycin linker-drug in non-conjugated form, with (ii) a dilution medium that comprises water, acetonitrile, and acid to form the filterable composition of the present invention; which comprises 30% to 60% (v/v), preferably 35% to 55%, of said acetonitrile.

The aqueous solution of the ADC can arise from various sources. For example, the ADC aqueous solution may be drawn from the reaction medium where the conjugation reaction that joins the linker-drug to the antibody (or antigen binding fragment thereof) occurs, or from a subsequently purified or isolated conjugation reaction product, i.e., the duocarmycin ADC in purified form, e.g. as a lyophilized product.

The optional free duocarmycin linker-drug in these ADC aqueous solutions is typically unreacted linker-drug. As the conjugation reaction often uses a molar excess of linker-drug, purification to insure removal of any free duocarmycin linker-drug is often employed. Accordingly, aqueous solutions from these sources may be intended to monitor the extent of conjugation reaction or assess the purification protocol.

Another source of the ADC aqueous solution is drawing a sample from the final ADC drug substance or drug product. The ADCs are typically delivered as an injectable composition and thus the drug substance as well as the drug product is often in the form of an aqueous solution. The free duocarmycin linker-drug, if any, in such aqueous solutions can arise from incomplete removal during purification of the free duocarmycin linker-drug and/or from unintended cleavage of the duocarmycin linker-drug from the ADC. These sources may be from stability testing and/or reference samples to determine or monitor the stability of the ADC composition over time, e.g., confirm that free linker-drug is not being formed/cleaved under storage conditions.

Alternatively, the drug substance or drug product can be in lyophilized form (a "lyophilized product"). The lyophilized product is typically reconstituted with water to form an aqueous ADC solution. All or part of this reconstituted liquid composition can serve as the ADC aqueous solution. Another option is to combine directly the lyophilized product with the dilution medium of the invention without preparing an intermediate aqueous reconstituted solution.

As will be understood by workers skilled in the art, the ADC aqueous solution may contain additional ingredients, given the various sources of the solution, such as buffers, salts, sugars (e.g., mannitol), lyophilization caking agents, etc. Likewise, the lyophilized product may contain additional ingredients such as buffering agent, lyoprotectant, surfactant, stabilizer, etc.

Adding a single dilution medium to the ADC aqueous solution or a lyophilized product is a convenient way to form the filterable composition of the present invention. The dilution medium comprises water, acetonitrile, and acid in sufficient amounts so as to form the desired acetonitrile concentration; e.g., of from 30% to 60% (v/v), preferably of from 35% to 55%, and most preferably of 40%. By adding sufficient quantities of the dilution medium to form the desired acetonitrile concentration, the filterable composition of the invention is formed in a single step.

The composition of the invention can be filtered across a filter to form a filtrate that is substantially free of the ADC. As used within the present invention, the term "substantially free" refers to a filtrate which comprises no more than 1% of the amount of ADC present in the composition of the invention. Typically, the amount is 0.5% or less, more typically 0.2% or less and often 0.1% or less. For clarity, if the composition of the invention contained 2.5 mg/ml of the ADC, then no more than 1% or 0.025 mg/ml ADC can be present in the filtrate.

As will be understood by workers skilled in the art, the filter has a molecular weight cutoff from 3 to 6 times smaller than the molecular weight of the antibody or antigen-binding fragment. Practically, the filter has a molecular weight cutoff within the range of from 1 to 100 kDa, more preferably of from 3 kDa to 50 kDa, even more preferably of from 10 to 30 kDa. Particularly preferred for the ADCs of formula (I) is a filter with a molecular weight cutoff of 10 kDa.

The filtering technique is not particularly limited; though generally centrifugal filtration is considered the most convenient. Gravity filtration could be used, but such takes more time to complete. Various commercial centrifugal filtration devices are known and available. For example, the PALL Corporation makes the Nanosep® (Omega) and Microsep® Centrifugal Devices. These devices differ in the volume size of the sample that is filtered. For the present invention, the smaller Nanosep® size is often preferred (e.g. a volume of 0.5 mL). Typically, the duration of the centrifugation is from 10 to 30 minutes and the speed is from 12,000 to 15,000 g.

Any suitable filter material that permits the separation of the ADC from the corresponding free duocarmycin linker-drug may be used in the present invention and can be determined by workers skilled in the art. Some filter materials are more robust than others in that the organic solvent (acetonitrile) can cause damage to the filter. This damage may result in the filter material being unsuitable for the separation, e.g., causing holes or leaks that permit too much leakage of the ADC through the filter. Commercial filter material typically comprises a membrane made of modified nylon, hydrophilic polypropylene, polyethersulfone material, or modified polyethersulfone material. For purposes of the present invention, a preferred filter material comprises a modified polyethersulfone material, such as the commercially available Nanosep® Omega filter media available from PALL Corp.

Before the filtration takes place, it may be useful to homogenize the composition. The homogenization may be performed with any suitable device that allows a uniform distribution of acetonitrile within the composition. The homogenization may further facilitate the separation via mere filtration of the duocarmycin-containing ADC from the free duocarmycin linker-drug.

After the composition of the invention is applied to the filter, the liquid that comes through the filter, i.e., the "filtrate," will be substantially free of the ADC of formula (I). The filtrate can then be analysed for duocarmycin linker-drug to determine, if any, and optionally what concentration is present in the filtrate. Any suitable technique can be used. Typically, a (liquid) chromatographic process is used, such as high performance liquid chromatography (HPLC) or ultra-high performance liquid chromatography (UPLC). Typically, the chromatography employed is reverse phase; e.g., reverse phase high performance liquid chromatography (RP-HPLC) or, more preferably, reverse phase ultra-high performance liquid chromatography (RP-UPLC). As is known to the person skilled in the art, selecting suitable chromatographic conditions, including the column packing material, the mobile phase, the gradient to be used, and the general loading/binding conditions and elution conditions are a matter of routine skill. For the detection of duocarmycin linker-drug in non-conjugated form any suitable detector may be used in the present invention. Typically, a UV detector is used. Advantageously, UPLC coupled with a UV detector provides a good solution for the analysis of samples comprising a small amount of duocarmycin linker-drug in non-conjugated form.

The measurement of the amount, if any, of duocarmycin linker-drug in non-conjugated form present in said filtrate (quantitative determination) is typically correlated to the amount of free duocarmycin linker-drug contained in the aqueous solution. By using the composition of the invention in the filtering process to obtain a filtrate substantially free of the ADC, the chromatographic separation and detection can have a limit of quantitation for the free linker-drug of 0.2 μg/mg of ADC, or less. That is, by correlating the quantitative determination to the original ADC aqueous solution, e.g., drug substance, the amount of free linker-drug can be determined down to at least 0.2 μg per 1 mg of ADC. Indeed, the limit of quantitation can be lower, such as 0.1 μg/mg or 0.01 μg/mg, etc.

A special application of the present invention relates to a method of releasing/approving an ADC batch, which comprises:

1) Obtaining a sample from an ADC batch, wherein said batch comprises an antibody conjugated with a duocarmycin linker-drug and optionally duocarmycin linker-drug in non-conjugated form;
2) Combining said sample with a dilution medium which comprises water, acetonitrile, and acid to form a filterable composition which comprises 30% to 60% (v/v), preferably 35% to 55%, of said acetonitrile;
3) Filtering said filterable composition to obtain a filtrate that is substantially free of said ADC;
4) Analysing said filtrate and determining whether said filtrate contains said duocarmycin linker-drug in non-conjugated form below a predetermined level; and 5) Releasing/approving said ADC batch if said duocarmycin linker-drug in non-conjugated form is below said predetermined level.

As used herein the term "antibody-drug conjugate batch" or "ADC batch" refers to the production, on commercial scale, of an ADC which has completed all processing stages so that it is in purified form and optionally containing excipients such as those suitable for a parenteral formulation or a lyophilized product. Practically, a batch size for an ADC is normally at least 30 L. Regulatory authorities, such as EMA, FDA, etc., require such a commercial batch of a pharmaceutical product to meet various purity and quality standards. For an ADC, one of those purity standards is the amount of free linker-drug. The above method incorporates the composition of the invention and its advantageous use in separating the duocarmycin ADC from the free duocarmycin linker-drug to better detect the presence, if any, of such free linker-drug. Accordingly, the filtrate is analysed, generally by RP-UPLC, to determine if the amount of non-conjugated duocarmycin linker-drug is below the regulatory limit (i.e., the "predetermined level"). The predetermined level is generally quite low and often requires a maximum amount of free duocarmycin linker-drug relative to the amount of ADC of 0.2 µg/mg, preferably of 0.1 µg/mg, more preferably of 0.02 µg/mg. The determination of the predetermined level can be by numerical value or as a limit of detection (LOD) test. In the latter case, limit of detection may be at, or less than, the predetermined level and hence a negative result (no free linker-drug) is considered to meet (be less than) the predetermined level. A similar strategy can be employed using the limit of quantification (LOQ), wherein the presence of the free linker-drug is observed but it is below the limit of quantification. Because the limit of quantification is at or below the predetermined level, any detected amount below the limit of quantification is considered to be below the predetermined level. In either case, the batch may be approved even though a numerical value is not determined because the amount is nonetheless below the predetermined limit.

Once a sample shows that the amount of non-conjugated duocarmycin linker-drug is below the predetermined level, then the ADC batch can be released or approved for sale, shipping, use by patients, etc. The term "releasing/approving" in the context of the invention refers to the satisfaction of the ADC batch with respect to at least the free duocarmycin linker-drug requirement. A sample that was above the predetermined level of free duocarmycin linker-drug would not be suitable for release into clinical trials or approvable as a commercial pharmaceutical (not eligible for sale or use). Such a batch would not be released or approved. Normally, a pharmaceutical product must pass many quality measurements and a failure of any one of them would block the final release or approval. Thus, the releasing/approving as used in the present invention context refers to gaining release or approval of the ADC product batch with respect to the free duocarmycin linker-drug content and not necessarily the final or ultimate release and/or approval of the batch.

Although the foregoing invention has been described in detail for the purpose of determining whether the filtrate contains the duocarmycin linker-drug in non-conjugated form, it is readily apparent to those of ordinary skill in the art that an analogous method may be applied for determining other impurities. In particular, the composition and filtering thereof are useful for providing a sample wherein duocarmycin linker-drug related impurities can be measured. The term "duocarmycin linker-drug related impurities" as used in the current invention refers to impurities which may arise from the degradation of the duocarmycin linker-drug during the synthesis, purification, and storage of the duocarmycin-containing ADC drug substance and drug product. These small molecule impurities typically with molecular weights of <2,000 Da (the molecular weight of a typical linker-drug) may also lead to toxicity and thus regulatory authorities may establish a maximum threshold (or predetermined level) for one or more of such impurities. With the method of the current invention the presence and the quantitative determination of these impurities may be established.

The following examples are intended to illustrate the scope of the present invention but not to limit it thereto.

EXAMPLES

Material and Methods

Trastuzumab duocarmazine (SYD985) and linker-drug vc-seco-DUBA (SYD980) were obtained using materials and procedures described in WO2011/133039. Reagents, solvents and buffers were procured from commercial suppliers.

Samples and blank samples were prepared as described below.

Sample Preparation or Blank Preparation

100 µL of a sample comprising the duocarmycin-containing ADC (10 mg/mL) and maybe some duocarmycin linker-drug in non-conjugated form were taken using a pipette and were introduced on a 10K filter (Nanosep® Omega Centrifugal Device). 300 µL of a dilution medium comprising a solution of 53% of acetonitrile in Milli-Q water and 0.13% formic acid were added on the filter. The sample and the dilution medium were homogenized (e.g. using vortex) on the filter and centrifuged for 15 min at 14,000 g and the filtrate was homogenized (e.g. using vortex) and transferred to an HPLC vial.

The Blank preparation followed the same procedure as described above but 100 µL of Milli-Q water instead of a sample comprising the duocarmycin-containing ADC and duocarmycin linker-drug in non-conjugated form was used.

External Standard Sample Preparation

External standard samples were used for the calculation of the concentration of the duocarmycin linker-drug in non-conjugated form in the sample. The external standard samples were prepared with 0.25 µg/mL of duocarmycin linker-drug in non-conjugated form.

RP-UPLC

For analytical purposes 10 µL of HPLC vial sample or HPLC blank vial sample was injected onto a reverse phase ultra high performance liquid chromatography (RP-UPLC) column of octadecyl (C18) derived silica with iso-butyl side chains and with TMS endcapping (Kinetex 1.7 µm, XB-C18 100 Å, 100×2.1 mm, Phenomenex) at a flow rate of 0.5 mL/min and at a column temperature of 45° C. The elution method is depicted in Table 1 below. The composition of mobile phase A was 0.1% formic acid in Milli-Q water, the composition of mobile phase B was 0.1% formic acid in acetonitrile/methanol 50/50 V/V. A reverse phase ultra performance liquid chromatography (UPLC) system equipped with a UV-detector with a 10 mm analytical cell was used. Absorbance was measured at 325 nm. Peak areas were determined using Waters Empower software. The amount of duocarmycin linker-drug in non-conjugated form was quantified using formula (VI), $$C_{L-D}[\mu g/mL] = \frac{A_{L-D} \times C_{std} \times N}{A_{std}}. \qquad (VI)$$

$C_{L-D}$ is the concentration of the duocarmycin linker-drug in non-conjugated form in the sample, $A_{L-D}$ is the peak area of the duocarmycin linker-drug in non-conjugated form in the sample, $C_{std}$ is the concentration of the duocarmycin linker-drug in non-conjugated form in the external standard, N is the dilution factor of the sample, $A_{std}$ is the average (average of at least 3 runs) peak area of the duocarmycin-containing linker-drug in non-conjugated form in the external standard.

The amount of duocarmycin-related impurities is calculated with formula (VII), $$C_i[\mu g/mL] = \frac{A_i \times C_{std} \times N}{A_{std} \times RRF_i}. \qquad (VII)$$

$C_i$ is the concentration of the duocarmycin-related impurities in the sample, $A_i$ is the peak area of the duocarmycin-related impurities in the sample, $C_{std}$ is the concentration of the duocarmycin linker-drug in non-conjugated form in the external standard, N is the dilution factor of the sample, $A_{std}$ is as defined above and $RRF_i$ is the Relative Response Factor of the duocarmycin-related impurities.

TABLE 1

Gradient program

| Time [min] | Mobile phase A [%] | Mobile phase B [%] |
| --- | --- | --- |
| 0 | 95 | 5 |
| 0.5 | 95 | 5 |
| 4.0 | 45 | 55 |
| 6.5 | 41 | 59 |
| 10.5 | 5 | 95 |
| 11.5 | 5 | 95 |
| 12.0 | 95 | 5 |
| 14.5 | 95 | 5 |

Example 1—External Standard Sample

The duocarmycin linker-drug vc-seco-DUBA in non-conjugated form (SYD980) (0.25 µg/mL) was analysed with the RP-UPLC method discussed above. FIG. 1 is a representation of the chromatogram obtained thereby. FIG. 1 shows a clear peak corresponding to the non-conjugated duocarmycin linker-drug (vc-seco-DUBA) at 6.205 minutes.

Example 2—Analysis of ADC

Figure 2:
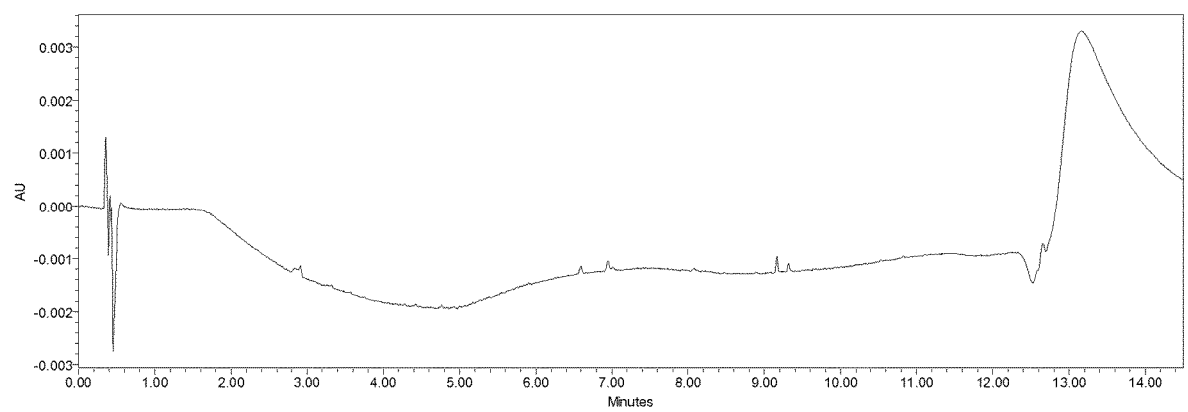
FIG. 2 represents the chromatogram from Example 2 wherein a sample from a trastuzumab duocarmazine batch was analysed and found to have no detectable free duocarmycin linker-drug and was thus a batch meeting the releasing/approving condition.

A sample from a trastuzumab duocarmazine batch was treated following the above Sample preparation procedure and analysed with the RP-UPLC method discussed above. The chromatogram obtained showed no presence of the non-conjugated linker-drug vc-seco-DUBA. FIG. 2 is a representation of the chromatogram thus obtained and no peak is detected at 6.2 minutes or in the vicinity thereof. The analysis determined that the amount of free duocarmycin linker-drug in the sample was below the limit of detection and thus below the predetermined level (i.e., a pass/fail detection test). Releasing/approving the batch was thus appropriate.

Example 3—Comparison of Compositions

100 µL of a sample comprising trastuzumab duocarmazine (10 mg/mL) and vc-seco-DUBA (0.25 µg/mL) was introduced on a 10K filter (Nanosep® Omega Centrifugal Device). On the filter was added a dilution medium (300 µL) which comprised water, acetonitrile (ACN) or methanol (MeOH) used in different percentages and acid (formic acid, trifluoroacetic acid (TFA), or hydrochloric acid) in various percentages. The sample and the dilution medium were homogenized on the filter and centrifuged for 15 min at 14,000 g. The filtrate was homogenized and transferred to an HPLC vial. The amount of vc-seco-DUBA (SYD980, i.e., the non-conjugated duocarmycin linker-drug) in the filtrate was detected by RP-UPLC-UV using the gradient program as depicted in Table 1 and quantified using formula (VI). The results are summarized in Table 2.

TABLE 2

Recovery results of vc-seco-DUBA

| Experiment | Organic solvent | Organic content (%) | Acid | Acid content (%) | Recovery (%) | RSD[a] (n = 3) (%) |
| --- | --- | --- | --- | --- | --- | --- |
| First experiment series | | | | | | |
| 1 | ACN | 40 | Formic acid | 0.1 | 86 | 2.4 |
| 2 | ACN | 40 | TFA | 0.1 | 95 | 1.8 |
| 3 | MeOH | 40 | Formic acid | 0.1 | 0 | — |
| Second experiment series | | | | | | |
| 4 | ACN | 25 | Formic acid | 0.1 | 12 | 8.1 |
| 5 | ACN | 30 | Formic acid | 0.1 | 36 | 9.7 |
| 6 | ACN | 35 | Formic acid | 0.1 | 68 | 0.7 |
| 7 | ACN | 40 | Formic acid | 0.1 | 82 | 2.3 |
| 8 | ACN | 50 | Formic acid | 0.1 | 87 | 1.2 |
| 9 | ACN | 50 | TFA | 0.1 | 90 | 1.5 |
| 10 | ACN | 55 | Formic acid | 0.1 | 87 | 5.6[b] |
| Third experiment series | | | | | | |
| 11 | ACN | 40 | HCl | 0.1 | 90 | 2.6 |
| 12 | ACN | 40 | Formic acid | 0.01 | 84 | 1.6 |
| 13 | ACN | 40 | Formic acid | 0.1 | 88 | 1.0 |
| 14 | ACN | 40 | Formic acid | 1.0 | 91 | 2.2 |

[a]Relative standard deviation for 3 samples
[b]Only two samples used in the average and RSD as the third had ADC leakage to an extent that the sample was excluded.

The first experiment series shows that acetonitrile facilitates the separation via mere filtration of trastuzumab duocarmazine from its non-conjugated duocarmycin linker-drug vc-seco-DUBA. Optimal recoveries of vc-seco-DUBA were obtained when using 40% of acetonitrile in combination with formic acid or trifluoroacetic acid. No recovery of vc-seco-DUBA could be obtained when methanol was used instead of acetonitrile.

Figure 3:
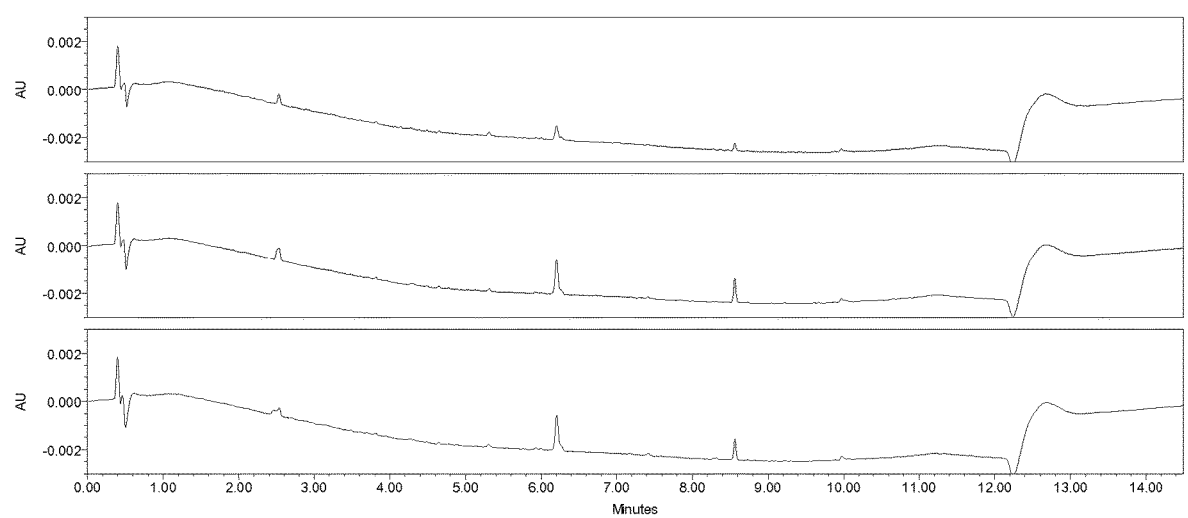
FIG. 3 represents three chromatograms from Example 3 wherein the percentage of acetonitrile is increased as the chromatograms descend such that the top chromatogram was formed using 30% acetonitrile, the middle using 40% acetonitrile, and the bottom using 55% acetonitrile.

The second experiment series shows that an increase in the quantity of acetonitrile is beneficial for the vc-seco-DUBA recovery, which goes from 12% (at 25% acetonitrile) to 90% (at 50% acetonitrile). The recovery obtained is acceptable if the acetonitrile is at least 30%. FIG. 3 represents chromatograms obtained from experiment 5 (30%

ACN), experiment 1 (40% ACN), and experiment 10 (55% ACN), respectively, in descending order. As can be seen graphically the peak at around 6.2 minutes, which corresponds to the amount of free duocarmycin linker-drug that is recovered, increases as the percentage of ACN increases.

The third experiment series further explored the effect of the type or amount of acid. The results indicate that the type or the amount of the acid is not critical but it is sufficient that the composition has a pH below 7.

The invention claimed is:

1. A method, which comprises:
   (a) combining (i) an aqueous solution or a lyophilized product of an antibody-drug conjugate of formula (I):

$$Ab\text{-}(L\text{-}D)_m \quad (I),$$

wherein Ab is an IgG antibody, L-D is a duocarmycin linker-drug, wherein the duocarmycin linker-drug in non-conjugated form is represented by formula (IV):

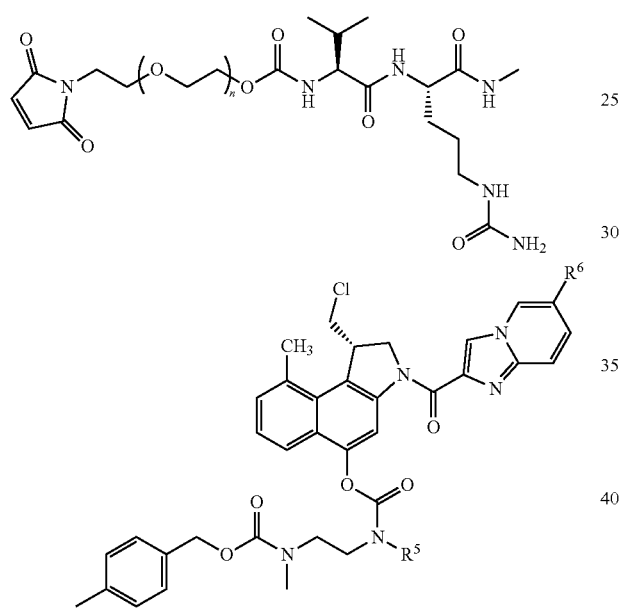

(IV)

wherein n is 0-3; $R^5$ is selected from

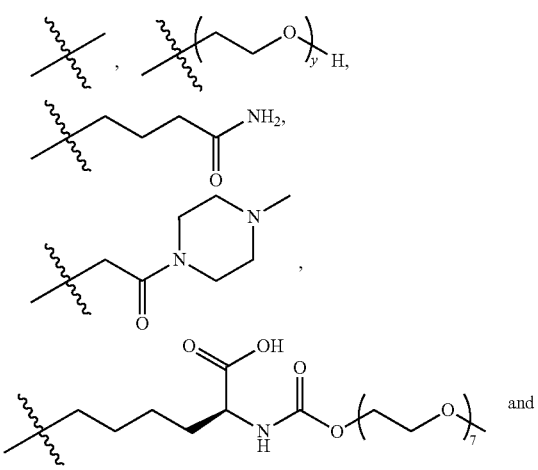

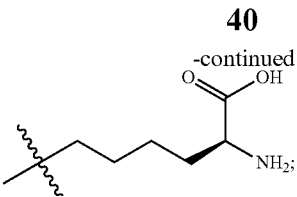

y is 1-16; and $R^6$ is selected from

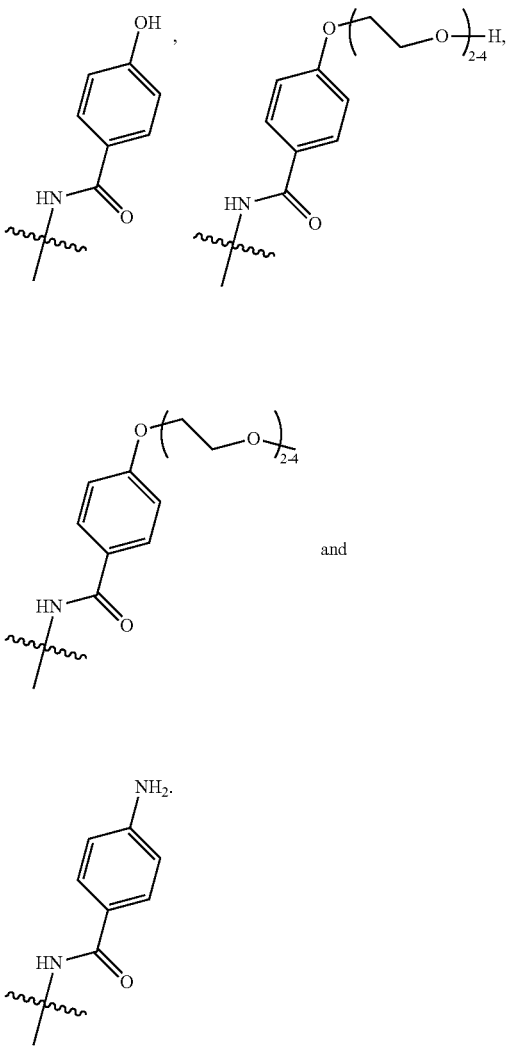

m represents an average DAR of from 1 to 12, and optionally further comprising the duocarmycin linker-drug in non-conjugated form, with (ii) a dilution medium that comprises water, acetonitrile, and acid to form a filterable composition, wherein said filterable composition comprises 30% to 60% (v/v) of said acetonitrile; and (b) filtering said filterable composition across a filter having a molecular weight cutoff within the range of 3 kDa to 50 kDa to form a filtrate.

2. The method according to claim 1, wherein said non-conjugated duocarmycin linker-drug is represented by the formula

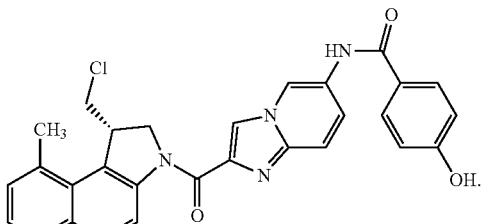
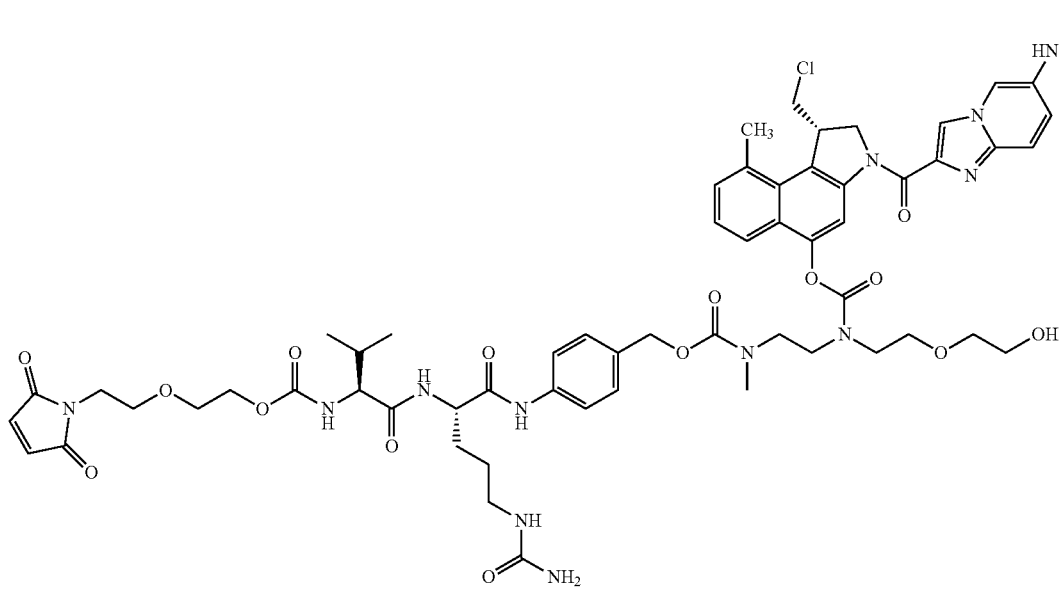

3. The method according to claim 1, wherein said filtrate is formed with less than 0.5% of the amount of said antibody-drug conjugate that was present in said filterable composition.

4. The method according to claim 3, wherein said filtering is centrifugal filtering.

5. The method according to claim 4, wherein said filter comprises a modified polyethersulfone filter media.

6. The method according to claim 1, which further comprises subjecting said filtrate to a chromatographic separation process suitable for isolating said duocarmycin linker-drug in non-conjugated form and measuring the amount, if any, of said duocarmycin linker-drug in non-conjugated form present in said filtrate.

7. The method according to claim 1, wherein said filterable composition comprises 35% to 55% of said acetonitrile.

8. The method according to claim 1, wherein said antibody-drug conjugate is contained in a concentration of from 0.5 to 50 mg/ml.

9. The method according to claim 8, wherein said antibody-drug conjugate is contained in a concentration of from 1.0 to 10 mg/ml.

10. The method according to claim 1, wherein said acid in said filterable composition has a concentration of from 0.05% to 2%.

11. The method according to claim 10, wherein said acid in said filterable composition has a concentration of from 0.1% to 1%.

12. The method according to claim 11, wherein said acid is selected from the group consisting of trifluoroacetic acid, formic acid, and hydrochloric acid.

13. The method according to claim 9, wherein said filtrate is formed with less than 0.2% of the amount of said antibody-drug conjugate that was present in said filterable composition.

14. The method according to claim 13, wherein said filtrate is formed with less than 0.1% of the amount of said antibody-drug conjugate that was present in said filterable composition.

15. The method according to claim 1, wherein said filter has a molecular weight cutoff within the range of 10 kDa to 30 kDa.

* * * * *